(12) United States Patent
Mensonides-Harsema et al.

(10) Patent No.: US 11,304,936 B2
(45) Date of Patent: Apr. 19, 2022

(54) SULFASALAZINE SALTS, PRODUCTION PROCESSES AND USES

(71) Applicant: MEDAC GESELLSCHAFT FUER KLINISCHE SPEZIALPRAEPARATE MBH, Wedel (DE)

(72) Inventors: Marguerite Mensonides-Harsema, Houston, TX (US); Sebastian Bialleck, Wedel (DE)

(73) Assignee: MEDAC GESELLSCHAFT FUER KLINISCHE SPEZIALPRAEPARATE MBH

( * ) Notice: Subject to any disclaimer, the term of this patent is extended or adjusted under 35 U.S.C. 154(b) by 31 days.

(21) Appl. No.: 16/766,660

(22) PCT Filed: Nov. 23, 2018

(86) PCT No.: PCT/EP2018/082330
§ 371 (c)(1),
(2) Date: May 22, 2020

(87) PCT Pub. No.: WO2019/101903
PCT Pub. Date: May 31, 2019

(65) Prior Publication Data
US 2020/0360356 A1    Nov. 19, 2020

(30) Foreign Application Priority Data
Nov. 23, 2017  (EP) ................................ 17203275

(51) Int. Cl.
*A61K 31/4402* (2006.01)
*A61K 9/00* (2006.01)
*A61K 45/06* (2006.01)
*C07D 213/76* (2006.01)

(52) U.S. Cl.
CPC ........ *A61K 31/4402* (2013.01); *A61K 9/0031* (2013.01); *A61K 9/0053* (2013.01); *A61K 45/06* (2013.01); *C07D 213/76* (2013.01); *C07B 2200/13* (2013.01)

(58) Field of Classification Search
CPC .................................................. A61K 31/4402
See application file for complete search history.

(56) References Cited

U.S. PATENT DOCUMENTS

| 2,396,145 A | 3/1946 | Askeloef .................. 260/156 |
| 10,703,723 B2 * | 7/2020 | Mensonides-Harsema ................ A61P 37/00 |
| 2006/0045865 A1 | 3/2006 | Jacob et al. ............... 424/78.27 |

FOREIGN PATENT DOCUMENTS

| CN | 106279008 | 1/2017 | ........... C07D 213/76 |
| EP | 1 101 490 | 5/2001 | ............... A61K 9/30 |
| GB | 564990 | 10/1944 | |
| GB | 1166684 | 10/1969 | ............. C09B 43/00 |
| WO | WO 97/22596 | 6/1997 | ........... C07D 239/94 |
| WO | WO 97/30035 | 8/1997 | ........... C07D 239/94 |
| WO | WO 97/32856 | 9/1997 | ........... C07D 239/94 |
| WO | WO 98/13354 | 4/1998 | ........... C07D 239/94 |
| WO | WO 99/02166 | 1/1999 | ............. A61K 31/66 |
| WO | WO 00/40529 | 7/2000 | ........... C07C 13/547 |
| WO | WO 00/41669 | 7/2000 | |
| WO | WO 01/92224 | 12/2001 | ........... C07D 209/42 |
| WO | WO 02/04434 | 1/2002 | ........... C07D 295/16 |
| WO | WO 02/08213 | 1/2002 | ......... C07D 295/185 |

OTHER PUBLICATIONS

Clegg et al. CAS: 126: 112913, 1996.*
U.S. Appl. No. 16/766,665, filed May 22, 2020, Mensonides-Harsema.
International Search Report and Written Opinion issued in PCT/EP2018/082330, dated Feb. 22, 2019, 16 pages.
International Preliminary Report on Patentability issued in PCT/EP2018/082330, dated May 26, 2020, 11 pages.
International Search Report and Written Opinion issued in PCT/EP2018/082331, dated Mar. 11, 2019, 10 pages.
International Preliminary Report on Patentability issued in PCT/EP2018/082331, dated May 26, 2020, 8 pages.
Matasic R, et al., "Maturation of Human Dendritic Cells as Sulfasalazine Target."; Croatian Medical Journal, Aug. 2001; 42(4): 440-445, 6 pages.
P Gadangi, et al.; "The anti-inflammatory mechanism of sulfasalazine is related to adenosine release at inflamed sites.", Journal of Immunology, Mar. 1, 1996, 156 (5) 1937-1941, abstract only, 3 pages.
Couto D. et al, "Scavenging of reactive oxygen and nitrogen species by the prodrug sulfasalazine and its metabolites 5-aminosalicylic acid and sulfapyridine." Redox Report. 2010;15(6):259-67. doi: 10.1179/135100010X12826446921707, abstract only, 2 pages.
Nygard, B.; Olofsson, J. and Sandberg, M.: "Some physico-chemical properties of salicylazosulphapyridine, including its solubility, protolytic constants and general spectrochemical and Polarographic behavior.", Acta Pharmaceutica Suecica 3: 313-342, Jul. 13, 1966, 30 pages.

(Continued)

Primary Examiner — Rei Tsang Shiao
(74) Attorney, Agent, or Firm — Hayes Soloway P.C.

(57) ABSTRACT

Disclosed are a process for preparing new crystal salt forms of sulfasalazine, in particular crystal Form A of the D(-)-N-methylglucamine (meglumine) salt of sulfasalazine (see FIG. 1), crystal form A of the piperazine salt of sulfasalazine (see FIG. 2) and crystal Form B of the diethylamine salt of sulfasalazine (see FIG. 4), and a pharmaceutical composition containing one or more of the inventive crystal salt forms in particular in the treatment of a disease or condition in which modulation of inflammatory cells is beneficial, a disease or condition concerning bones or joints and/or the gastro-intestinal tract.

10 Claims, 4 Drawing Sheets

(56) References Cited

OTHER PUBLICATIONS

Mohamed et al.; "Structural and Thermal Characterization of Cerium, Thorium and Uranyl Complexes of Sulfasalazine" Spectrochimica Acta Part A Molecular Biomolecular Spectroscopy 62 (4-5), 1095-1101. Jun. 13, 2005, abstract only, 2 pages.

Lindbergh Ed, Clary David: "ESCA applied to liquids. ESCA spectra from molecular ions in solution", Chemical Physics Letters, Elsevier BV, NL, vol. 39, No. 1, Apr. 1, 1976, pp. 8-10, XP 009503440.

Dahan et al; "Small intestinal efflux mediated by MRP2 and BCRP shifts sulfasalazine intestinal permeability from high to low, enabling its colonic targeting"; American Journal of Physiology—Gastrointestinal and Liver Physiology Published 2009 vol. 297 No. 2, G371-G377, 7 pages.

Liang et al.; "Evaluation of an accelerated Caco-2 cell permeability model."; J Pharm Sci. Mar. 2000; 89(3): 336-45, abstract only, 2 pages.

\* cited by examiner

SULFASALAZINE SALTS, PRODUCTION PROCESSES AND USES

TECHNICAL FIELD

The present invention relates to new crystal salt forms of sulfasalazine, in particular crystal Form A of the D(−)-N-methylglucamine (meglumine) salt of sulfasalazine (see FIG. 1), crystal form A of the piperazine salt of sulfasalazine (see FIG. 2) and crystal Form B of the diethylamine salt of sulfasalazine (see FIG. 4), which can be obtained by use of the inventive preparation process, a pharmaceutical composition comprising one or more of the inventive crystal salt forms in particular in the treatment of a disease or condition in which modulation of inflammatory cells is beneficial, a disease or condition concerning bones or joints and/or the gastro-intestinal tract.

BACKGROUND OF THE INVENTION

The compound known under the generic name sulfasalazine (also known as (3Z)-6-oxo-3-[[4-(pyridin-2-ylsulfamoyl)phenyl]hydrazinylidene]cyclohexa-1,4-diene-1-carboxylic acid (IUPAC); 2-hydroxy-5-[2-[4-[(2-pyridinylamino)sulfonyl]phenyl]diazenyl]-benzoic acid (CA index name)) was first described in U.S. Pat. No. 2,396,145 (GB 564990) and is highly effective in the treatment of different autoimmune diseases, e.g. rheumatoid arthritis, juvenile idiopathic arthritis, ankylosing spondylitis, ulcerative colitis and Crohn's disease.

Sulfasalazine forms brownish-yellow crystals (molecular weight 398.39 g/mol). The melting point is specified with 240° C. to 245° C. (U.S. Pat. No. 2,396,145). The solubility of sulfasalazine in water is less than 5 mg/100 ml. The substance has four theoretical $pk_{a/b}$ values, which are at 0.6, 2.4, 9.7 and 11.8. It has been proven to be very difficult to produce hydrate- and solvate-free salts of sulfasalazine by using established methods.

The structure of sulfasalazine ((3Z)-6-oxo-3-[[4-(pyridin-2-ylsulfamoyl)phenyl]hydrazinylidene]cyclohexa-1,4-diene-1-carboxylic acid (IUPAC); 2-hydroxy-5-[2-[4-[(2-pyridinylamino)sulfonyl]phenyl]diazenyl]-benzoic acid (CA index name)) is shown below:

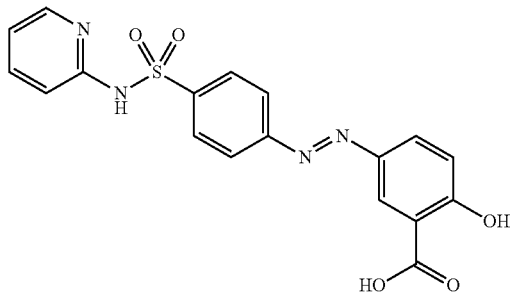 [SMILES: O=C(O)c1cc(/N=N/c2ccc(S(=O)(=O)Nc3ccccn3)cc2)ccc1O]

Sulfasalazine is a well-established active pharmaceutical ingredient and used in anti-inflammatory therapy. Sulfasalazine is used in the treatment of active rheumatoid arthritis, the treatment of active juvenile idiopathic oligoarthritis, the treatment of active juvenile idiopathic polyarthritis and spondyloarthropathy with peripheral arthritis in humans. Sulfasalazine is further used as a prodrug of 5-aminosalicylic acid in the treatment of inflammatory bowel diseases such as Crohn's disease and ulcerative colitis. In adults, guided by tolerability to and efficacy of, sulfasalazine is generally administered orally as tablets at doses of 500 to 4000 mg per day.

Sulfasalazine is one of the most widely used disease-modifying antirheumatic drugs (DMARD) and is also used in combination with glucocorticoids and/or in combination with other small molecule DMARDs such as methotrexate and/or hydroxychloroquine and/or biological DMARDs such as TNF-alpha relevant biologics.

The mechanism of action of sulfasalazine and its metabolites 5-aminosalicylic acid and sulfapyridine is partially still unknown. Sulfasalazine and/or its metabolites have anti-inflammatory and immune modulating properties in vivo and in vitro at a variety of (inflammatory) cell types such as T-cells, dendritic cells, macrophages, natural killer cells, epithelial cells, B-cells and mast cells through different biological "pathways". It has been shown, for example, that sulfasalazine-treated dendritic cells cannot stimulate T-cells through inhibition of the NF-kB pathway (Matasic R, Dietz A B, Vuk-Pavlovic S.; "Maturation of human dendritic cells as sulfasalazine target."; Croat Med J 2001 August; 42(4): 440-5). In addition it has been demonstrated that sulfasalazine inhibits the binding of TNF-alpha to its receptor in 125I-TNF-alpha displacement studies. Furthermore it has been shown, that sulfasalazine, like methotrexate enhances adenosine release through the inhibition of AICAR transformylase and thus diminishes inflammation (P Gadangi, M Longaker, D Naime, R I Levin, P A Recht, M C Montesinos, M T Buckley, G Carlin and B N Cronstein; "The anti-inflammatory mechanism of sulfasalazine is related to adenosine release at inflamed sites.", J Immunol Mar. 1, 1996, 156 (5) 1937-1941). The well-established antioxidant effects of sulfasalazine in association to its inhibitory effects over neutrophil oxidative burst have been shown to be exerted both through its scavenging effects against reactive oxygen and nitrogen species as well as its metal chelating properties (Couto D1, Ribeiro D, Freitas M, Gomes A, Lima J L, Fernandes E., Redox Rep. 2010; 15(6):259-67. doi: 10.1179/135100010X12826446921707, "Scavenging of reactive oxygen and nitrogen species by the prodrug sulfasalazine and its metabolites 5-aminosalicylic acid and sulfapyridine.").

However, due to the low solubility of sulfasalazine (0.03 mg/mL in de-ionized water at 24° C.) and the current known pharmaceutical compositions of sulfasalazine the systemic bioavailability of sulfasalazine in man is low (about 15 to 20% of an oral dose is absorbed in the small intestine) and the pharmacokinetic intra- and inter-variability is high ($C_{max}$ is 4 to 12 hours, with a median peak concentration at 6 hours). Non-absorbed sulfasalazine is transformed by aza-reducing gut flora to 5-aminosalicylic acid (systemic bioavailability from 10 to 30%) and sulfapyridine (systemic bioavailability to about 60%). The metabolites can be detected in blood plasma after about 10 hours. The half-life of intravenously administered sulfasalazine is approximately 7.6±3.6 hours.

Apart from biotransformation of sulfasalazine by the gut flora in the lower intestine, sulfasalazine is also metabolized in the liver to the metabolites 5-aminosalicylic acid and sulfapyridine. In the liver the primary metabolite sulfapyridine is acetylated prior to excretion, wherein the speed is determined by the acetylation phenotype. Therefore, the half-life of sulfapyridine may vary from 10.4 to 14.8 hours (depending on fast or rather slow acetylators).

The most common side reactions associated with sulfasalazine are anorexia, headache, nausea, vomiting, gastric distress, and apparently reversible oligospermia, tiredness, dizziness, fever, asthenia, insomnia and vertigo might also affect the patient during medication with sulfasalazine.

But also gastrointestinal reactions including hepatitis, hepatic failure, pancreatitis, bloody diarrhea, impaired folic acid absorption, impaired digoxin absorption, stomatitis, diarrhea, abdominal pains, and neutropenic enterocolitis might come up during medication.

Also the skin (e.g. skin rash or itching, urtikaria, increased sensitivity to sunlight), the blood/lymphaitc system (aplastic anemia, agranulocytosis, leukopenia, megaloblastic (macrocytic) anemia, purpura, thrombocytopenia, hypoprothrombinemia, methemoglobinemia, congenital neutropenia, and myelodysplastic syndrome) or the central nervous system (transverse myelitis, convulsions, meningitis, transient lesions of the posterior spinal column, cauda equina syndrome, Guillain-Barre syndrome, peripheral neuropathy, mental depression, vertigo, hearing loss, insomnia, ataxia, hallucinations, tinnitus, and drowsiness) might be influenced. Occuring hepatobiliary disorders might be hepatotoxicity, including elevated liver function tests (SGOT/AST, SGPT/ALT, GGT, LDH, alkaline phosphatase, bilirubin), jaundice, cholestatic jaundice, cirrhosis, hepatitis cholestatic, cholestasis and possible hepatocellular damage including liver necrosis and liver failure. Some of these cases were fatal.

The low rate of resorption of sulfasalazine is one reason for the high amount of 500 mg sulfasalazine per single solid oral dosage form, which has to be administered to the patient, in order to obtain a sufficient exposure to the drug sulfasalazine and thus obtain sufficient clinical effect. High amounts of drug substance and/or the big size of the tablets, however, result in a poor patient's compliance and unnecessary high rate of adverse events partly due to unfavorable ratios of sulfasalazine and its metabolites in vivo.

In the manufacture of pharmaceutical compositions, it is important that the active compound is in a form in which it can be conveniently handled and processed in order to obtain a commercially-viable manufacturing process. In this connection, the chemical stability and the physical stability of the active compound are important factors. The active compound, and compositions containing it, must be capable of being effectively stored over appreciable periods of time, without exhibiting any significant change in the physicochemical characteristics (e.g. chemical composition, density, water content and solubility) of the active compound.

Thus, it would be beneficial to provide a solvate free crystal form of sulfasalazine exhibiting solubility properties. From prior art it has become evident that it is very difficult to produce and/or isolate solvate-free crystals of sulfasalazine with simultaneous improved properties like solubility.

It is known, that sulfasalazine has metal chelating properties in vivo. However, the mono salts of sulfasalazine with counterions sodium and potassium, although mentioned in Nygard et al. (Nygard, B.; Olofsson, J. and Sandberg, M.: "Some physicochemical properties of salicylazosulphapyridine, including its solubility, protolytic constants and general spectrochemical and Polarographic behavior.", Acta Pharmaceutica Suecica 3: 313-342 (1966)) have never been isolated. The hemi salts of sulfasalazine with metal counterions like strontium (as its trihydrate), calcium (as its trihydrate), magnesium (as its trihydrate) are less soluble than sulfasalazine. Other metal complexes (cerium, thorium and uran) of sulfasalazine with ammonium have been examined as well (G G Mohamed et al. Spectrochim Acta A Mol Biomol Spectrosc 62 (4-5), 1095-1101. 2005 Jun. 13; "Structural and Thermal Characterization of Cerium, Thorium and Uranyl Complexes of Sulfasalazine"). These counterions, however, are pharmaceutically not acceptable.

Conformational analysis of sulfasalazine salts with different counter ions like Mg, Sr, Ca and Zn shows that the terminal pyridine ring displays some oriental flexibility, which indicates a propensity for conformational polymorphism of sulfasalazine salts.

Patent application GB 1,166,684 discloses alkoxy-amine addition salts of sulfasalazine. According to the patent the prepared alkoxy-amine addition salts of sulfasalazine are difficult to crystallize in that they are obtained as viscous oils which only crystallize upon stirring with ether or alcohol; a number of the disclosed salts are very hygroscopic and/or have a high water content. For example, the N-methl-(1)-D-glucosamine salt (also known as meglumine salt, which is used hereinafter) of sulfasalazine identified in GB 1,166,684 and prepared by adding a solution of methylglucamine in hot methylglycol to a solution of sulfasalazine in 2-methoxyethanol, exhibits, after extensive drying, a water content of 9%. Such a moisture content is in particular unsuitable for producing stable pharmaceutical compositions.

Due to their unfavorable physicochemical characteristics (hygroscopicity and/or high water content and/or poor solubility and/or pharmaceutical unacceptability) none of the prior disclosed sulfasalazine salts have been considered suitable for the use in pharmaceutical compositions.

CN 106 279 008 A relates to the technical field of purification process of sulfasalazine (5-[p-(2-pyridylaminosulfonyl)benzene]azo-salicylic acid. Sulfasalazine is purified by using specific amine salts of sulfasalazine as intermediate products and precipitating sulfasalazine from a solution containing the specific amine salt. According to example 6, a specific diethylamine salt of sulfasalazine is prepared as intermediate product and the sulfasalazine is subsequently precipitated from the solution. The applicant has prepared the diethylamine salt sulfasalazine intermediate in accordance with the description as provided in example 6 of CN 106 279 008 A. In addition the resulting diethylamine salt of sulfasalazine has been evaluated by an X-ray powder diffractogram (XRPD), which proved that the resulting diethylamine sulfasalazine product is present as crystal Form A of the diethylamine salt of sulfasalazine according to FIG. 3.

Thus, there is still a need to provide a pharmaceutical composition of sulfasalazine with an increased bioavailability of sulfasalazine and/or solubility of sulfasalazine and/or improved risk-benefit ratio of the pharmaceutical sulfasalazine composition, in particular due to a decreased degree of adverse events and/or an improved patient compliance.

BRIEF DESCRIPTION OF THE INVENTION

The problem of the present invention is solved by the subjects of the independent claims. Advantages (preferred embodiments) are set out in the detailed description hereinafter including the figures as well as in the dependent claims.

Accordingly, a first aspect of the present invention relates to a process for preparing crystalline organic salts of 2-hydroxy-5-[2-[4-[(2-pyridinylamino)sulfonyl]phenyl]diazenyl]-benzoic acid (sulfasalazine), wherein the organic salts are selected from diethylamine, piperazine and D-(−)-N-methylglucamine (meglumine), the process comprising or consisting of the following steps:

A1. Providing sulfasalazine free acid form in a suitable solvent,

B1: Providing an organic amine containing constituent selected from meglumine and piperazine in a suitable solvent, C1: Mixing the sulfasalazine solution of step A1) with the organic amine containing constituent solution of step B1) at room temperature, preferably 19° C. to 25° C., and D1: Separating the crystals of Form A piperazine sulfasalazine or solvates thereof or the crystals of Form A meglumine sulfasalazine or solvates thereof formed in the solution of step C1), or A2: Providing sulfasalazine free acid form in a suitable solvent, B2: Providing an organic amine containing constituent from meglumine and diethylamine, in a suitable solvent, C2: Mixing the sulfasalazine solution of step A2) with the organic amine containing constituent solution of step B2), wherein the amine containing constituent has a molar excess with respect to sulfasalazine of at least 5%, more preferably at least 10%, more preferably at least 20%, and D2a: Concentrating the mixed solution formed in step C2) and separating the crystals of Form A meglumine sulfasalazine or solvates thereof of the crystals of Form B diethylamine sulfasalazine or solvates thereof or D2b: Adding a further solvent to the mixed solution formed in step C2, wherein the further solvent is different from the solvents used in step A2 and B2 and separating the crystals of Form A meglumine sulfasalazine or solvates thereof of the crystals of Form B diethylamine sulfasalazine or solvates thereof, with the proviso that the inventive method does not cover crystal Form A of diethylamine sulfasalazine.

A second aspect of the present invention relates to inventive crystals of Form A meglumine sulfasalazine, crystals of Form A piperazine sulfasalazine or crystals of Form B diethylamine sulfasalazine respectively obtainable according to the inventive preparation process.

A third aspect of the present invention relates to a pharmaceutical composition comprising a therapeutically effective amount of one or more of the inventive crystal salt forms of sulfasalazine.

A fourth aspect of the present invention relates to a use of an inventive crystal salt form of sulfasalazine or an inventive pharmaceutical composition in the preparation of a medicament for/in the treatment of i) A human disease or condition in which modulation of inflammatory cells is beneficial, ii) A disease or condition concerning bones or joints, preferably selected from the group consisting of arthritis associated with or including osteoarthritis/osteoarthrosis, both primary and secondary to, for example, congenital hip dysplasia; cervical and lumbar spondylitis, and low back and neck pain; rheumatoid arthritis and Still's disease; sero-negative spondyloarthropathies including ankylosing spondylitis, psoriatic arthritis, reactive arthritis and undifferentiated spondarthropathy, septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositis and polymyositis; polymyalgia rheumatic; juvenile arthritis including idiopathic inflammatory arthritis of whatever joint distribution and associated syndromes, and rheumatic fever and its systemic complications; vasculitis including giant cell arteritis, Takayasu's arteritis, Churg-Strauss syndrome, polyarteritis nodos, microscopic polyarteritis, and vasculitis associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthralgias, tendonitis, and myopathies; and iii) A disease or condition concerning gastro-intestinal tract, preferably selected from the group consisting of eosinophilic gastro-enteritis, mastocytosis, Crohn's disease, colitis including ulcerative colitis, proctitis; coeliac disease, irritable bowel syndrome, and food-related allergies which may have effects remote from the gut, e.g. migraine, rhinitis or eczema.

A fifth aspect of the present invention relates to a method of treating i) A human disease or condition in which modulation of inflammatory cells is beneficial, ii) A disease or condition concerning bones or joints, preferably selected from the group consisting of arthritis associated with or including osteoarthritis/osteoarthrosis, both primary and secondary to, for example, congenital hip dysplasia; cervical and lumbar spondylitis, and low back and neck pain; rheumatoid arthritis and Still's disease; sero-negative spondyloarthropathies including ankylosing spondylitis, psoriatic arthritis, reactive arthritis and undifferentiated spondarthropathy, septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositis and polymyositis; polymyalgia rheumatic; juvenile arthritis including idiopathic inflammatory arthritis of whatever joint distribution and associated syndromes, and rheumatic fever and its systemic complications; vasculitis including giant cell arteritis, Takayasu's arteritis, Churg-Strauss syndrome, polyarteritis nodos, microscopic polyarteritis, and vasculitis associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthralgias, tendonitis, and myopathies; and iii) A disease or condition concerning gastro-intestinal tract, preferably selected from the group consisting of eosinophilic gastro-enteritis, mastocytosis, Crohn's disease, colitis including ulcerative colitis, proctitis; coeliac disease, irritable bowel syndrome, and food-related allergies which may have effects remote from the gut, e.g. migraine, rhinitis or eczema in a patient suffering from, or at risk of, said disease or condition, which comprises administering to the patient a therapeutically effective amount of an inventive crystal salt form of sulfasalazine or an inventive pharmaceutical composition.

The aspects of the present invention as set out hereinbefore can also comprise, if reasonable to a person skilled in the art, any possible combination of the preferred embodiments as set out in the dependent claims or disclosed in the following detailed description and figures.

DETAILED DESCRIPTION OF THE INVENTION

Figure 1:
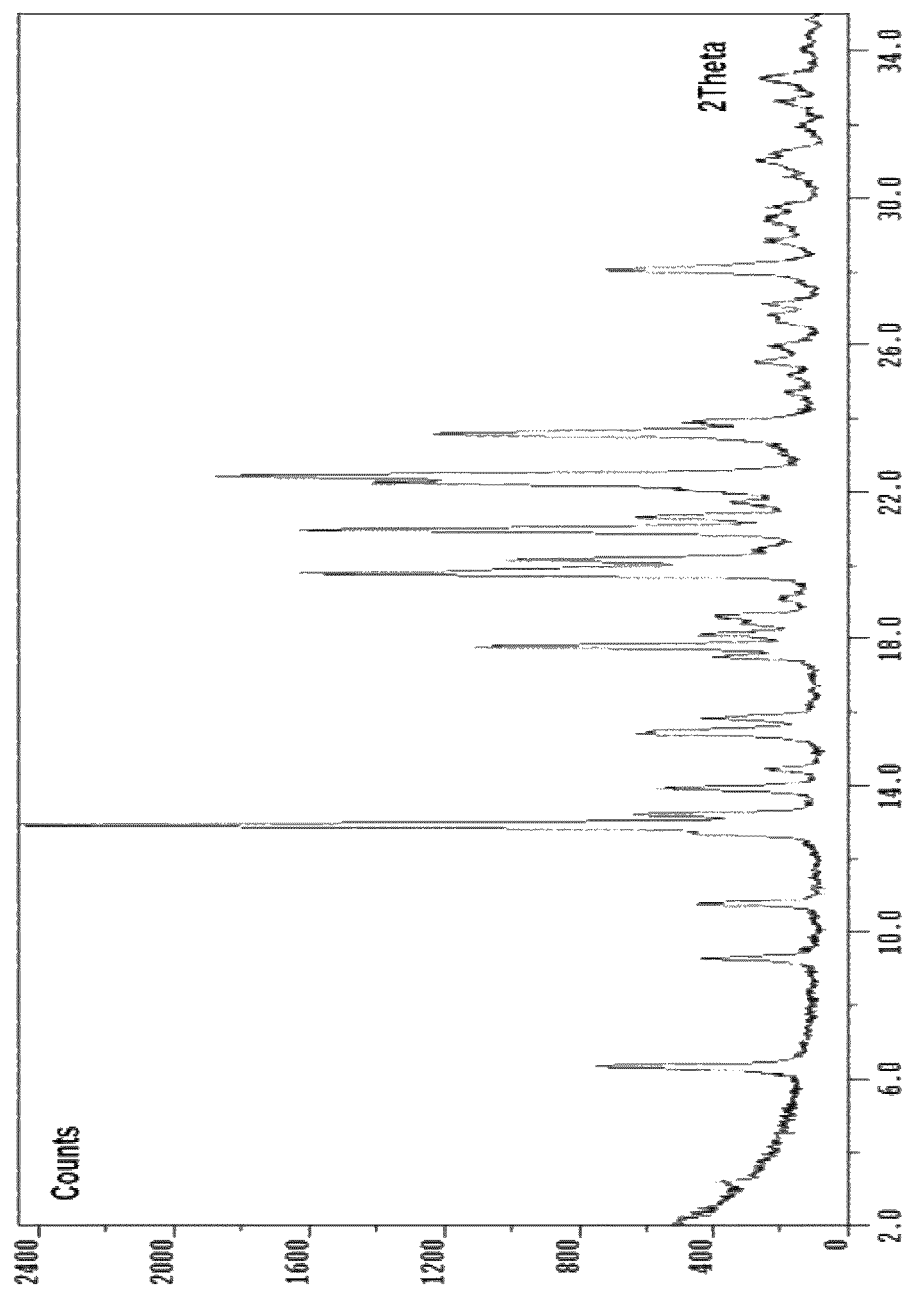
FIG. 1 represents an X-ray powder diffraction pattern of crystal Form A of the meglumine salt of sulfasalazine

The present inventors have found out that the new and inventive crystal salt forms of sulfasalazine, in particular crystal Form A of the D(−)-N-methylglucamine (meglumine) salt of sulfasalazine (see FIG. 1), crystal Form A of the piperazine salt of sulfasalazine (see FIG. 2) and crystal Form B of the diethylamine salt of sulfasalazine (see FIG. 4) display a favorable pharmacokinetic profile compared to the free acid form of sulfasalazine: decreased $t_{max}$, increased $C_{max}$ and increased F (bioavailability) (see Example 7 below).

Furthermore, the present inventors found out that while sulfasalazine free acid form is characterized as a low intestinal absorption compound (see Arik Dahan, Gordon L. Amidon; "Small intestinal efflux mediated by MRP2 and BCRP shifts sulfasalazine intestinal permeability from high to low, enabling its colonic targeting"; American Journal of Physiology—Gastrointestinal and Liver Physiology Published 21 Jul. 2009 Vol. 297 no. 2, G371-G377) having a low permeability through Caco-2 cell monolayers (Liang E1, Chessic K, Yazdanian M.; "Evaluation of an accelerated Caco-2 cell permeability model."; J Pharm Sci. 2000 March; 89(3):336-45), the inventive crystal salt forms of sulfasalazine instead display an improved permeability through Caco-2 cell monolayers as compared to free acid form of sulfasalazine. According to an alternative or cumulative embodiment concerning all aspects of the present invention the apparent permeability coefficient for the transport from the apical to the basal side of the inventive crystal forms of sulfasalazine, preferably of crystal Form A of the meglumine salt of sulfasalazine is increased by a factor ≥0.5, ≥1.0, ≥1.5, ≥2.0, ≥2.5, ≥3.0 or ≥3.5 compared to the free acid form of sulfasalazine (see Example 6 below).

In addition, the free acid form of sulfasalazine is classified according to the United States Pharmacopoeia as practically insoluble (<0.1 mg/mL), having a solubility in de-ionized water at 24° C. of 0.031 mg/mL. According to measurements conducted by the present inventors the sulfasalazine free acid form exhibits a solubility of 0.06 mg/mL in de-ionized water at 24° C., while the inventive crystal salt forms of sulfasalazine exhibit an increased solubility in de-ionized water at 24° C. of generally ≥0.1 mg/mL, more preferably ≥0.5 mg/mL, ≥1 mg/mL, ≥5 mg/mL, ≥10 mg/mL, ≥15 mg/mL, ≥20 mg/mL, ≥25 mg/mL, ≥30 mg/mL or ≥35 mg/mL. According to an alternative measurement, the inventive crystal forms of sulfasalazine, in particular crystal Form A of the meglumine salt of sulfasalazine exhibits a solubility in de-ionized water at 22° C. and pH 6.6 of ≥50 mg/mL, ≥60 mg/mL, ≥70 mg/mL, ≥80 mg/mL, ≥90 mg/mL, ≥100 mg/mL (see example 8 below).

Thus, due to the increased bioavailability and/or solubility a decreased dose of sulfasalazine may be used in therapeutic treatment of a disease or a condition in which modulation of inflammatory cells is beneficial that require systemic exposure to sulfasalazine, e.g. rheumatoid arthritis, ankylosing spondylitis and juvenile idiopathic arthritis, without altering the total systemic exposure to sulfasalazine. This leads to an improved risk-benefit profile due to a decreased exposure to sulfapyridine, the metabolite which is generally held responsible for some of the adverse events seen in patients treated with sulfasalazine (adverse events are exemplified in the background section of the present application). Particularly, slow-acetylating patients will benefit from the decreased exposure to sulfapyridine. Furthermore, compliance to the therapy may be improved due to the decreased burden of the therapy through the use of fewer and/or smaller solid pharmaceutical compositions (e.g. tablets, micro tablets, capsules, multiple unit pellet systems and the like).

In the context of the present invention, the term "inventive crystal salt forms of sulfasalazine" refers to crystalline organic salts of 2-hydroxy-5-[2-[4-[(2-pyridinylamino)sulfonyl]phenyl]diazenyl]-benzoic acid (sulfasalazine) obtainable by the inventive preparation process, in particular exemplified by crystal Form A of the D(−)-N-methylglucamine (meglumine) salt of sulfasalazine, crystal Form A of the piperazine salt of sulfasalazine and crystal Form B of the diethylamine salt of sulfasalazine.

According to the present invention, the phrase "crystal Form A of the D(−)-N-methylglucamine salt of sulfasalazine" may be used synonymously to "crystal Form A of the meglumine salt of sulfasalazine", "Form A meglumine salt", "Form A meglumine sulfasalazine" or "meglumine sulfasalazine salt".

According to the present invention, the phrase "crystal Form A of the piperazine salt of sulfasalazine" may be used synonymously to "crystal Form A of the piperazine salt of sulfasalazine", "Form A piperazine salt", "Form A piperazine sulfasalazine" or "piperazine sulfasalazine salt".

According to the present disclosure, the phrase "crystal Form A of the diethylamine salt of sulfasalazine" may be used synonymously to "crystal Form A of the diethylamine salt of sulfasalazine", "Form A diethylamine salt", or "Form A diethylamine sulfasalazine". The crystal Form A of diethylamine salt of sulfasalazine as such is not covered by the present invention.

According to the present invention, the phrase "crystal Form B of the diethylamine salt of sulfasalazine" may be used synonymously to "crystal Form B of the diethylamine salt of sulfasalazine", "Form B diethylamine salt", or "Form B diethylamine sulfasalazine". According to an optional alternative embodiment of the present invention, the crystal Form B of the diethylamine salt of sulfasalazine is not covered by the present invention.

According to another optional alternative embodiment of the present invention, any diethylamine salt of sulfasalazine is not covered by the present invention.

According to an embodiment of all aspects of the present invention, the inventive crystal salts of sulfasalazine are preferably at least 50 wt.-%, 60 wt.-%, 70 wt.-%, 80 wt.-%, 90 wt.-%, 95 wt.-%, 96 wt.-%, 97 wt.-%, 98 wt.-%, 99% or 100 wt.-% crystalline based on the total weight of the respective inventive salt form of sulfasalazine. Crystallinity can be estimated by conventional X-ray diffractometric techniques.

According to a further embodiment concerning all aspects of the present invention, crystal Form A of the meglumine salt of sulfasalazine exhibits at least the following characteristic X-ray powder diffraction (XRPD) peaks (expressed in degrees 2θ±0.2 degrees) (the margin of error being consistent with the United States Pharmacopeia general chapter on X-ray diffraction (USP941)—see the United States Pharmacopeia Convention. X-Ray Diffraction, General Test <941>. *United States Pharmacopeia*, 25$^{th}$ ed. Rockville, Md.: United States Pharmacopeial Convention; 2002: 2088-2089):

(1) 6.35, 13.93 and 22.41, or
(2) 9.31, 15.86 and 20.99, or
(3) 6.35, 13.93, 15.48, 15.86, 22.41 and 23.60, or
(4) 6.35, 10.79, 12.93, 13.93, 15.48, 15.86, 18.12, 19.82 and 22.41, or
(5) 9.31, 10.79, 12.93, 13.93, 14.47, 15.48, 15.86, 17.56, 19.10, 23.60 and 28.07, or
(6) 6.35, 12.93, 13.93, 14.47, 15.48, 15.86, 19.10, 19.82, 20.99, 21.27, 22.41, 23.60, 23.89 and 28.07, or
(7) 6.35, 9.31, 10.79, 12.93, 13.93, 14.47, 15.48, 15.86, 17.78, 18.12, 19.82, 20.11, 20.99, 21.27, 22.41, 23.60, 23.89, 28.07 and 28.80, or
(8) 6.35, 9.31, 10.79, 12.93, 13.93, 14.47, 15.48, 15.86, 17.56, 17.78, 18.12, 18.50, 19.10, 19.82, 20.11, 20.99, 21.27, 22.41, 23.60, 23.89, 24.70, 25.14, 25.55, 25.93, 26.81, 28.07 and 28.80, or
(9) 6.35, 9.31, 10.79, 12.93, 13.93, 14.47, 15.48, 15.86, 17.56, 17.78, 18.12, 18.50, 19.10, 19.82, 20.11, 20.99, 21.27, 22.41, 23.60, 23.89, 24.70, 25.14, 25.55, 25.93, 26.81, 28.07, 28.80, 29.49, 32.01, 32.58, 33.23.

According to a preferred embodiment concerning all aspects of the present invention, Form A meglumine salt exhibits at least the following characteristic XRPD peaks: 6.35, 13.93, 15.48, 15.86, 20.99, 22.41, 23.60 and 28.07.

In FIG. 1, a characteristic XRPD spectrum of inventive crystal Form A of meglumine salt of sulfasalazine is provided.

According to another alternative of cumulative embodiment concerning all aspects of the present invention crystal Form A of the piperazine salt of sulfasalazine exhibits at least the following characteristic X-ray powder diffraction (XRPD) peaks (expressed in degrees 2θ±0.2 degrees) (the margin of error being consistent with the United States Pharmacopeia general chapter on X-ray diffraction (USP941)—see the United States Pharmacopeia Convention. X-Ray Diffraction, General Test <941>. *United States Pharmacopeia*, 25$^{th}$ ed. Rockville, Md.: United States Pharmacopeial Convention; 2002: 2088-2089):

(1) 11.95, 12.30 and 16.42, or
(2) 12.30, 12.93 and 15.01, or
(3) 11.95, 12.30, 12.93, 16.42, 17.87 and 20.36, or
(4) 8.11, 11.95, 12.30, 15.01, 16.42, 17.87, 20.36 and 20.74, or
(5) 11.95, 12.30, 12.93, 15.01, 16.42, 17.87, 20.36, 20.74, 22.41 and 23.41 or
(6) 11.95, 15.01, 16.42, 17.87, 20.36, 20.74, 23.41, 24.01, 24.67, 24.99 and 26.09, or
(7) 8.11, 11.95, 12.30, 12.93, 15.01, 16.42, 17.87, 20.36, 20.74, 22.41, 23.41, 24.01, 24.67, 24.99 and 26.09, or
(8) 11.95, 12.30, 12.93, 15.01, 16.42, 17.87, 20.36, 20.74, 22.41, 23.41, 24.01, 24.67, 24.99, 26.09, 26.81, 27.73 and 28.80, or
(9) 8.11, 11.95, 12.30, 12.93, 15.01, 16.42, 17.87, 20.36, 20.74, 22.41, 23.41, 24.01, 24.67, 24.99, 26.09, 26.81, 27.73, 28.80, 29.80 and 30.43.

According to a preferred embodiment concerning all aspects of the present invention, the Form A piperazine salt exhibits at least the following characteristic XRPD peaks: 12.30, 12.93, 15.01, 16.42, 22.41 and 23.41.

Figure 2:
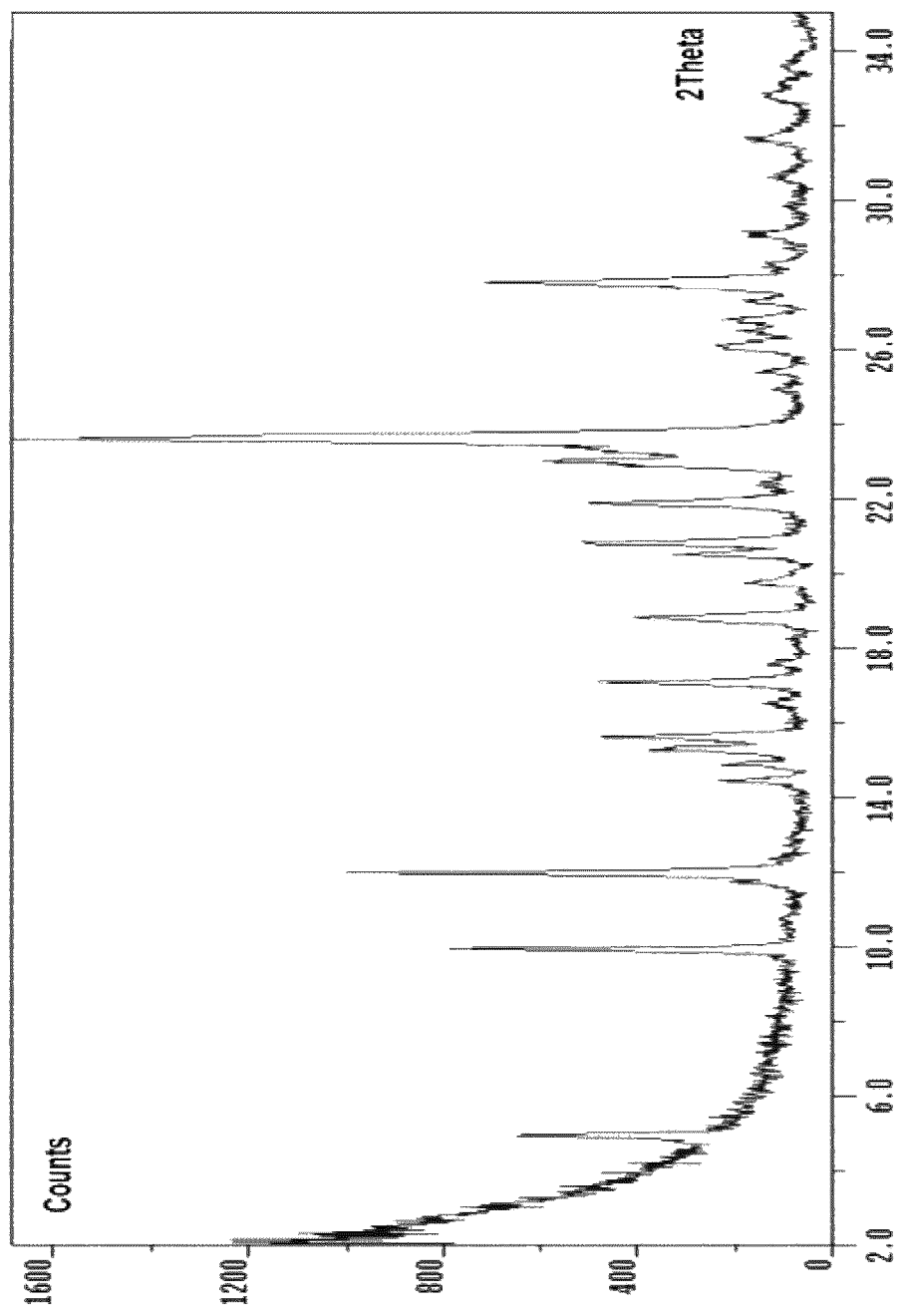
FIG. 2 represents an X-ray powder diffraction pattern of crystal Form A of the piperazine salt of sulfasalazine

In FIG. 2, a characteristic XRPD spectrum of inventive crystal Form A of piperazine salt of sulfasalazine is provided.

Disclosed herein is also that crystal Form A of the diethylamine salt of sulfasalazine exhibits at least the following characteristic X-ray powder diffraction (XRPD) peaks (expressed in degrees 2θ±0.2 degrees) (the margin of error being consistent with the United States Pharmacopeia general chapter on X-ray diffraction (USP941)—see the United States Pharmacopeia Convention. X-Ray Diffraction, General Test <941>. *United States Pharmacopeia*, 25$^{th}$ ed. Rockville, Md.: United States Pharmacopeial Convention; 2002: 2088-2089):

(1) 7.16, 11.48, and 18.78, or
(2) 10.50, 15.41 and 21.87, or
(3) 7.16, 10.50, 11.48, 18.78, 21.65 and 21.87, or
(4) 10.50, 11.48, 12.42, 14.38, 15.41, 16.64, 18.78 and 21.87, or
(5) 7.16, 10.50, 11.01, 11.48, 13.87, 15.92, 16.64, 18.78, 21.08, 21.65 and 22.15, or
(6) 7.16, 10.50, 11.01, 11.48, 12.42, 13.87, 14.38, 15.41, 15.92, 16.64, 17.19, 18.28, 18.78, 21.08, 21.65, 21.87, and 22.15 or
(7) 7.16, 10.50, 11.48, 12.42, 13.87, 14.38, 15.41, 15.92, 16.64, 20.52, 21.08, 21.65, 21.87, 22.15, 22.47, 23.16, 23.63, 24.14 and 25.11, or
(8) 7.16, 10.50, 11.01, 11.48, 12.42, 13.87, 14.38, 15.41, 15.92, 16.64, 17.19, 18.28, 18.78, 20.52, 21.08, 21.65, 21.87, 22.15, 22.47, 23.16, 23.63, 24.14 and 25.11, or
(9) 7.16, 10.50, 11.01, 11.48, 12.42, 13.87, 14.38, 15.41, 15.92, 16.64, 17.19, 18.28, 18.78, 20.52, 21.08, 21.65, 21.87, 22.15, 22.47, 23.16, 23.63, 24.14, 25.11, 26.94, 27.95, 28.92, 29.46.

It is further disclosed that the Form A diethylamine salt exhibits at least the following characteristic XRPD peaks: 7.16, 10.50, 11.48, 18.78, 21.65 and 21.87.

Figure 3:
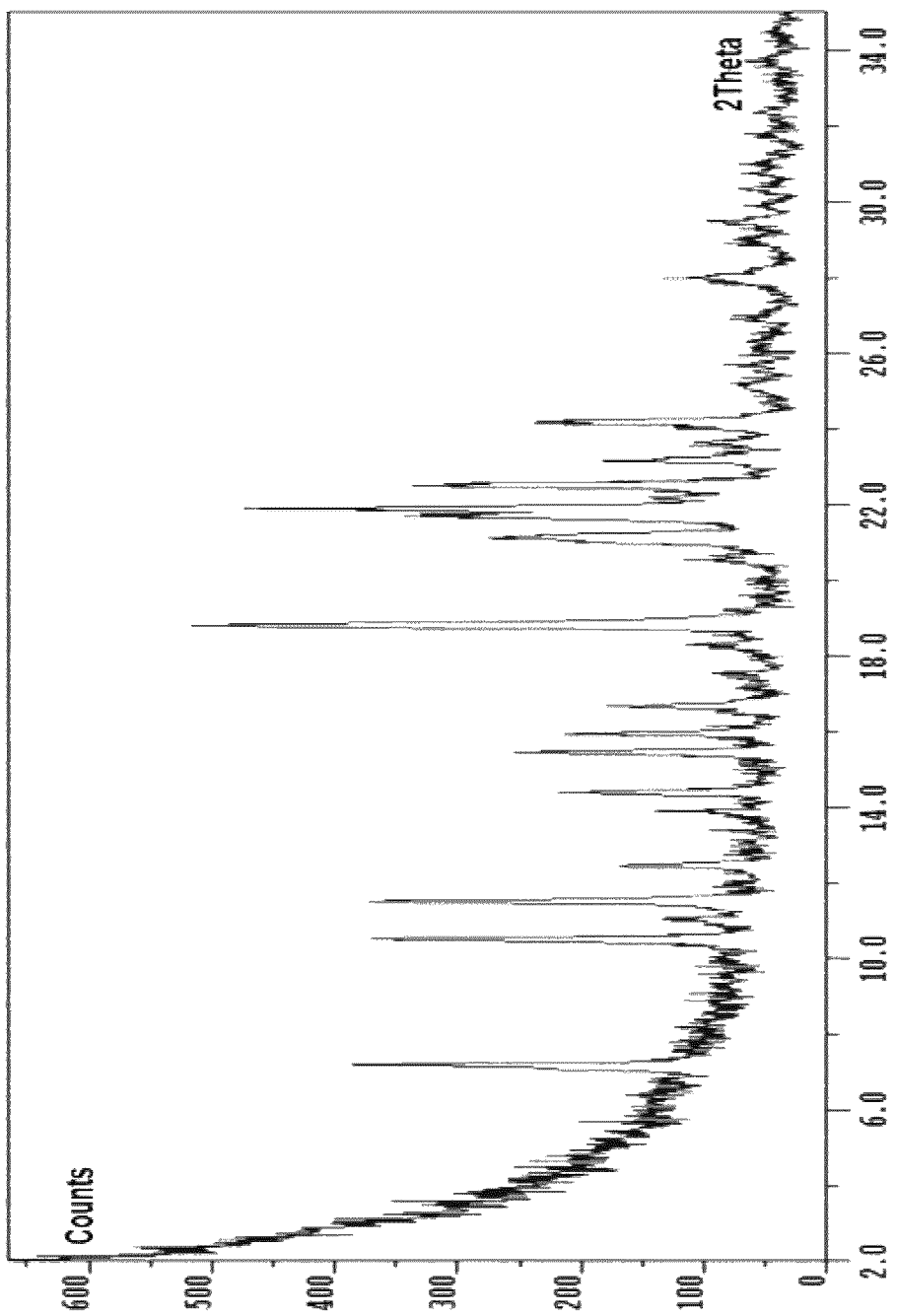
FIG. 3 represents an X-ray powder diffraction pattern of crystal Form A of the diethylamine salt of sulfasalazine

In FIG. 3, a characteristic XRPD spectrum of crystal Form A of diethylamine salt of sulfasalazine is provided.

According to an another alternative or cumulative embodiment concerning all aspects of the present invention a second polymorph crystal Form B of the diethylamine salt of sulfasalazine exhibits at least the following characteristic X-ray powder diffraction (XRPD) peaks (expressed in degrees 2θ±0.2 degrees) (the margin of error being consistent with the United States Pharmacopeia general chapter on X-ray diffraction (USP941)—see the United States Pharmacopeia Convention. X-Ray Diffraction, General Test <941>. *United States Pharmacopeia*, 25$^{th}$ ed. Rockville, Md.: United States Pharmacopeial Convention; 2002: 2088-2089):

(1) 6.85, 17.82 and 22.75, or
(2) 11.38, 20.58 and 23.98, or
(3) 6.85, 11.38, 17.62, 20.58 and 22.75, or
(4) 6.85, 11.38, 11.70, 17.62, 20.58, 22.75 and 23.98, or
(5) 11.38, 11.70, 15.29, 16.71, 17.62, 19.92, 20.58, 21.30, 22.75, 23.63 and 23.98, or
(6) 6.85, 11.38, 11.70, 14.78, 15.29, 15.70, 16.71, 17.62, 19.92, 20.20, 20.58, 21.30, 22.75, 23.63, 23.98 and 28.61 or (7) 6.85, 11.38, 11.70, 14.78, 15.29, 15.70, 16.71, 17.62, 19.92, 20.20, 20.58, 21.30, 22.75, 23.63, 23.98, 25.05, 25.71, 26.81, 27.95 and 28.61, or (8) 6.85, 11.38, 11.70, 14.78, 15.29, 15.70, 16.71, 17.62, 19.92, 20.20, 20.58, 21.30, 22.75, 23.63, 23.98, 25.05, 25.71, 26.81, 27.51, 27.95, 28.61, 29.14, 31.06.

According to a preferred embodiment concerning all aspects of the present invention, the Form B diethylamine salt exhibits at least the following characteristic XRPD peaks: 6.85, 11.38, 11.70, 17.62, 20.58, 22.75 and 23.98.

Figure 4:
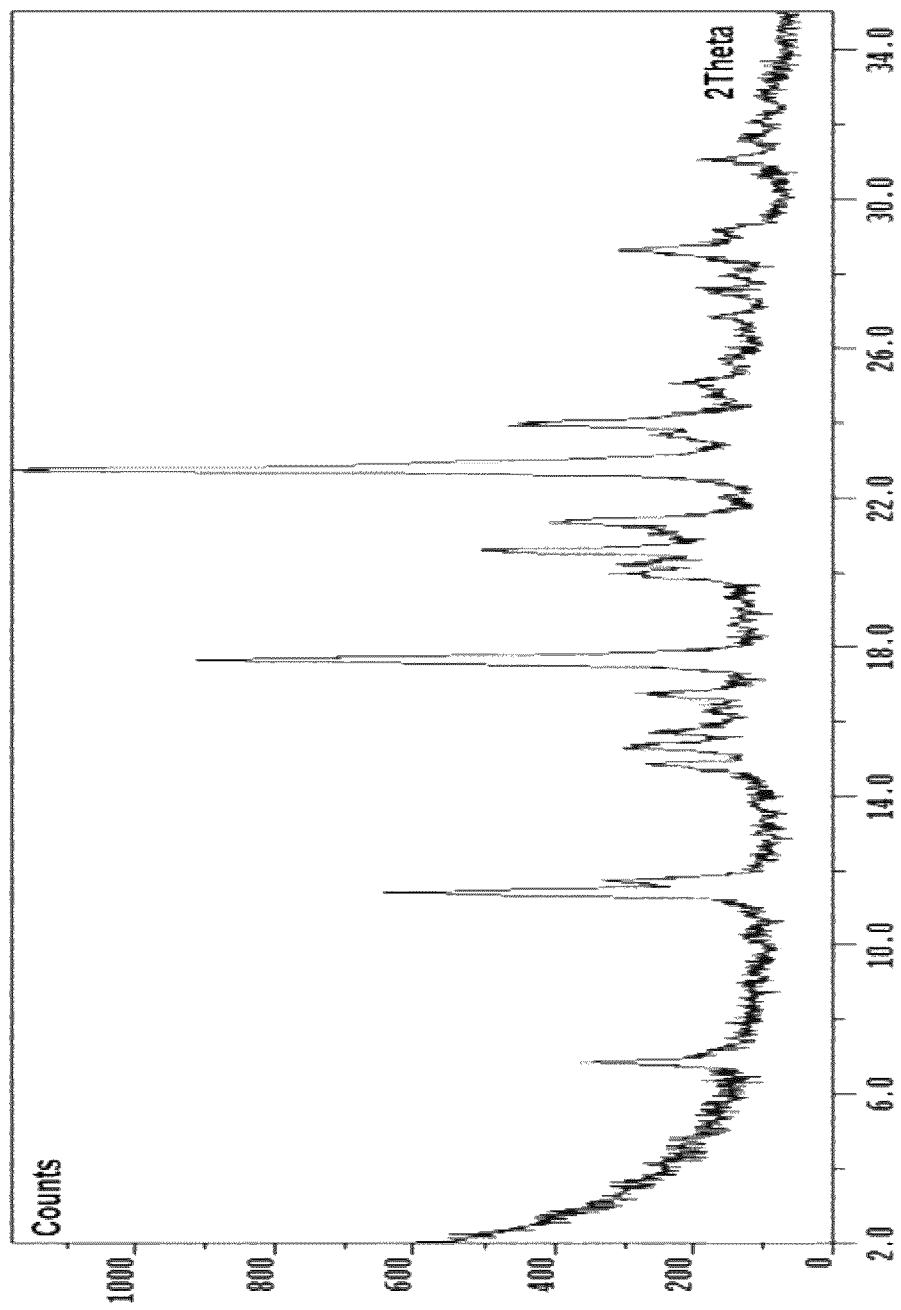
FIG. 4 represents an X-ray powder diffraction pattern of crystal Form B of the diethylamine salt of sulfasalazine

In FIG. 4, a characteristic XRPD spectrum of inventive crystal Form B of diethylamine salt of sulfasalazine is provided.

Although the inventive crystal salt forms of sulfasalazine, in particular crystal Form A of the D(−)-N-methylglucamine (meglumine) salt of sulfasalazine, crystal Form A of the piperazine salt of sulfasalazine and crystal Form B of the diethylamine salt of sulfasalazine, can be used as solvates or hydrates, the inventors found out that the inventive crystal salt forms of sulfasalazine can be obtained in solvate-free, in particular hydrate-free form by use of the inventive preparation process. Such a solvate-free, in particular hydrate-free (anhydrous) form may exhibit advantageous physico-chemical properties when manufacturing the pharmaceutical composition, as the solvate-free, in particular the anhydrous form supports in particular the physical and chemical stability of the active ingredient sulfasalazine and the pharmaceutical composition respectively over shelf life.

Thus, the inventive crystal salt forms of sulfasalazine, namely crystal Form A of the D(−)-N-methylglucamine (meglumine) salt of sulfasalazine, crystal Form A of the piperazine salt of sulfasalazine and crystal Form B of the diethylamine salt of sulfasalazine, enable a skilled person to manufacture a stable pharmaceutical composition, preferably a stable pharmaceutical oral dosage formulation, more preferably a stable pharmaceutical solid oral dosage formulation respectively comprising sulfasalazine as active ingredient. The term "stable" in the context of the present invention means that a measured value falls within range of specified values determined in accordance with a respective applicable regulatory guideline, e.g. the European Pharmacopeia.

The properties or the physical and chemical stability of the inventive pharmaceutical tablet composition may be tested in conventional manner, e.g. by measurement of appearance, hardness (or resistance to crushing), disintegration time, dissolution, friability, water content, assay for the inventive sulfasalazine salts and/or their degradation products (related substances), and/or uniformity of dosage units or mass after storage at controlled storage conditions; e.g. at intermediate and/or accelerated conditions according to ICH guideline Q1A(R2) (i.e. at 25° C./60% relative humidity (RH) and/or at 40° C./75% RH). These tests shall be performed according to applicable pharmaceutical regulatory standards as described e.g. in ICH or EMA guidelines and/or the European Pharmacopeia (EP).

At least some of these attributes, i.e. properties or physical and chemical stability, preferably most of these attributes and most preferably all of these attributes of the inventive pharmaceutical tablet composition are stable over time and different controlled storage conditions. According to a preferred embodiment the dissolution (profile) of the inventive pharmaceutical tablet composition according to the present invention, e.g. a tablet or film-coated tablet, is stable over at least 6 months when stored preferably in Alu-Alu blisters at intermediate or long-term storage conditions, i.e. 25° C./60% RH or 40° C./75% RH. More preferably, dissolution and further additional attributes such as, e.g., assay, related substances or uniformity of dosage units or mass are also stable after storage over at least 6 months when stored at intermediate or long-term storage conditions.

With regard to the ability (rate and extent) of water vapour uptake, the European Pharmacopoeia Technical guide 2015, General Chapter 5.11. has categorized pharmaceutical solids into four different classes: i.e. as slightly hygroscopic (equal to or greater than 0.2%, but less than 2% w/w uptake at RH 80% and 25° C.), hygroscopic (equal to or greater than 2%, but less than 15% w/w uptake at RH 80% and 25° C.), very hygroscopic (equal to or greater than 15% w/w uptake at RH 80% and 25° C.) and deliquescent (sufficient water is absorbed to form a liquid) according to the extent of water uptake.

The present inventors found furthermore out, that the inventive crystal salt forms of sulfasalazine, in particular Form A meglumine salt, Form A piperazine salt and/or Form B diethylamine salt, are classified as only slightly hygroscopic substances. According to an alternative or cumulative embodiment of all aspects of the present invention, the hygroscopicity of the inventive crystal salts of sulfasalazine, preferably the Form A meglumine salt, is generally ≤1% w/w, more preferably ≤0.5% w/w water vapor uptake at RH 80% and 25° C. Thus, the inventive crystal salt forms of sulfasalazine are suitable for preparing stable pharmaceutical compositions.

According to the first aspect of the present invention, the inventive process for preparing crystalline organic salt forms of sulfasalazine is provided.

According to step A1) of the inventive preparation process, sulfasalazine free acid form is provided in a suitable solvent. According to an alternative or cumulative embodiment of the present invention, the solvent in step A1) is generally selected from a suitable organic solvent, preferably selected from the group consisting of acetone, acetonitrile, and alcohol, such as methanol, ethanol, propanol, isopropanol, and butanol.

According to step B1) of the inventive preparation process, an organic amine containing constituent selected from meglumine, and piperazine, is provided in a suitable solvent. According to an alternative of cumulative embodiment of the present invention, the solvent in step B1) is preferably water or contains water.

According to step C1) of the inventive preparation process, the sulfasalazine solution of step A1) is mixed with the organic amine containing constituent solution of step B1) at room temperature, preferably at 19° C. to 25° C. According to an alternative of cumulative embodiment of the present invention, equimolar amounts of sulfasalazine free acid form and the organic amine containing constituent are used in step C1). According to a further alternative of cumulative embodiment of the present invention, the solution of sulfasalazine and organic amine containing constituent is mixed in step C1) for at least 24 hours at room temperature, preferably at least 48 hours at room temperature, more preferably at least 72 hours at room temperature, even more preferably at least 96 hours at room temperature.

According to step D1) of the inventive preparation process, the inventive crystal salt forms of sulfasalazine, preferably crystal Form A megulmine sulfasalazine salt, and crystal Form A piperazine sulfasalazine salt or solvates thereof, which are formed in the solution during step C1), are separated. According to a preferred embodiment of all aspects of the present invention, the inventive crystal salt forms of sulfasalazine are solvate free and in particular anhydrous. In the context of the present invention solvate free and or hydrate free (anhydrous) means, that respective inventive crystal salt form of sulfasalazine contains ≤9 wt.-%, ≤5 wt.-%, ≤4 wt.-%, ≤3 wt.-%, ≤2 wt.-%, ≤1 wt.-% solvate and/or water based on the total weight of the respective inventive crystal form of sulfasalazine. In case the separated inventive crystal salt forms of sulfasalazine in step D1) contain higher amounts of residue solvate/water, suitable drying steps can be conducted to render the inventive crystal salt form of sulfasalazine solvate free and/or hydrate free.

According to an alternative process for preparing inventive crystal salt forms of sulfasalazine, in particular the inventive crystal Form A meglumine sulfasalazine salt and the inventive crystal Form B diethylamine sulfasalazine salt, the sulfasalazine free acid form is provided according to step A2) in a suitable solvent and the organic amine containing constituent selected from meglumine and diethylamine, is provided according to step B2) in a suitable solvent. According to an alternative of cumulative embodiment of the alternative preparation process of the present invention the solvent in step A2) and B2) is generally independently selected from a suitable organic solvent, preferably selected from the group consisting of acetone, acetonitrile, and alcohol, such as methanol, ethanol, propanol, isopropanol, and butanol, more preferably the solvent used in step A2) and B2) is acetone.

According to the alternative process for preparing inventive crystal salt forms of sulfasalazine, the sulfasalazine solution of step A2) is mixed with the organic amine containing constituent solution of step B2), wherein according to step C2) the amine containing constituent has a molar excess with respect to sulfasalazine of at least 5%, more preferably at least 10%, more preferably at least 20%.

According to the alternative process for preparing inventive crystal salt forms of sulfasalazine, the solution of sulfasalazine and organic amine containing constituent is according to an alternative or cumulative process preferably mixed in step C2) at elevated temperatures, preferably in the range of 30° C. to 80° C., more preferably 40° C. to 65° C. According to a further alternative or cumulative embodiment of the alternative preparation process, the solution of sulfasalazine and organic amine containing constituent is mixed in step C2) for up to 24 hours.

According to step D2a) of the alternative process for preparing the inventive crystal salt forms the mixed solution formed in step C2) is concentrated and the crystals of or solvates thereof of the crystals of form A meglumine sulfasalazine or solvates thereof are separated.

Alternatively to step D2a) according to step D2b) of the alternative process for preparing the inventive crystal salt forms a further solvent may be added to the mixed solution formed in step C2), wherein the further solvent is different from the solvents used in step A2) and B2) and the crystals of Form A meglumine sulfasalazine or solvates thereof or the crystals of Form B diethylamine sulfasalazine or solvates thereof formed in D2b) are separated. According to an alternative or cumulative preferred embodiment the solution containing the further solvent in step D2b) is mixed for at least 24 hours at room temperature, preferably in the range of 19° C. to 25° C., preferably at least 48 hours at room temperature, more preferably at least 60 hours at room temperature. According to a further preferred embodiment, the solvent used in step A2) and B2) is acetone and the further solvent added during step D2b) is tert-butyl methylether.

In case the separated inventive crystal salt forms of sulfasalazine in step D2a) or D2b) contain amounts of residual solvate/water, suitable drying steps can be conducted to render the inventive crystal salt form of sulfasalazine solvate free and/or hydrate free.

According to the third aspect of the present invention a pharmaceutical composition is provided comprising a therapeutically effective amount of one or more of the inventive crystal salt forms of sulfasalazine as described in particular hereinbefore and the examples. The inventive pharmaceutical composition may comprise in addition to one or more of the inventive crystal salt forms of sulfasalazine one, two, three of more pharmaceutical acceptable adjuvants.

Depending on the mode of administration, the inventive pharmaceutical composition may comprise from 0.01 to 100 wt.-%, from 1 to 90 wt.-%, from 25 to 80 wt.-%, from 30 to 70 wt.-%, from 40 to 60 wt.-%, or 50 wt.-% of inventive crystal salt form of sulfasalazine respectively based on the total weight of the inventive pharmaceutical composition.

The inventive pharmaceutical composition may be administered systemically, e.g. by oral administration in the form of tablets, microtablets, granules, powders, capsules, syrups, or multi-unit pellet systems (so called MUPS); or by parenteral administration (e.g. intra venous, sub cutaneous, intra-articular) in the form of solutions or suspensions; or by rectal administration in the form of suppositories, foams or the like. Preferably the inventive pharmaceutical composition is administered orally.

In case the inventive pharmaceutical composition is administered orally, the inventive crystal salt forms of sulfasalazine in the inventive pharmaceutical composition is/are preferably protected from contact with acidic gastric juice, e.g., by an enteric coating layer provided on or within the inventive pharmaceutical composition.

According to one alternative embodiment of the inventive pharmaceutical composition one or more inventive crystal salt forms of sulfasalazine are mixed with one, two, three, four or more pharmaceutical tablet excipients and are compressed into a tableted dosage form. The one, two, three, four or more pharmaceutical tablet excipients are preferably selected from the group consisting of filler agents, binder agents, disintegrant agents, lubricant agents and the like and compressed into tablets.

The compressed inventive tablet is optionally covered/coated with one or more film forming agent(s), which may contain, e.g., alkaline substances, to obtain a smooth surface of the tablet and further enhance the stability of the tablet during packaging, transport and storage. Such a tablet coating layer may alternatively or cumulatively comprise additives like anti-tacking agents, colorant agents and pigments or other additives to obtain a tablet of good appearance. Alternatively or cumulatively, the inventive tablet composition may comprise an enteric coating layer, which protects the inventive crystal salt forms of sulfasalazine from contact with the gastric acid. Alternatively or cumulatively the inventive tablet composition may comprise pharmaceutical excipients, which facilitate immediate or sustained release of the inventive crystal salt forms of sulfasalazine. In particular, the tablet coating may comprise one, two, three, four, five or more constituents selected from the group consisting of cellulose derivatives, such as pre-gelatinized starch, cellulose ether (e.g. ethylcellulose (EC), methylcellulose (MC), hydroxyethyl cellulose (HEC) or hydroxypropyl cellulose (HPC); in particular cross-linked sodium carboxymethylcellulose) or ester o semiester of cellulose (e.g. cellulose acetate phthalate (CAP) or hydroxypropyl methylcellulose phthalate (HPMCP)); acrylic polymers or copolymers, preferably methacrylate aminoester copolymers (e.g. Eudragit RS or Eudragit RL) or methacrylic acid ethyl acrylate copolymer (e.g. methacrylic acid ethyl acrylate copolymer 1:1); waxy materials (e.g. carnauba wax); polyethylene glycols (e.g. Macrogol 6,000, Macrogol 20,000); (crosslinked) polyvinyl pyrrolidone (e.g. Povidon K30, Povidon K25, Crospovidon), polyvinyl alcohol or derivatives e.g. polyvinyl acetate phthalate (PVAP); pigments (e.g. titanium dioxide); stearic acid, magnesium stearate or glycerol mono stearate; and talcum.

According to an alternative embodiment of the inventive pharmaceutical composition for oral administration, the inventive composition is alternatively or cumulatively suitable for dispersion in an aqueous liquid with neutral or slightly acidic pH-value before being orally administered or fed through a naso-gastric tube.

According to a further alternative embodiment of the inventive pharmaceutical composition for oral administration, the inventive pharmaceutical composition may be provided in form of a hard or a soft capsule, preferably a soft gelatin capsule, wherein the inventive crystal salt forms of sulfasalazine may be admixed with, for example a vegetable oil or polyethylene glycol. Also liquid or semisolid preparations of the inventive crystal salt forms of sulfasalazine may be filled into hard gelatin capsules to form the inventive compositions.

When administered orally a single unit dose of the inventive pharmaceutical composition of all aspects of the present invention may generally comprise one or more inventive crystal salt forms of sulfasalazine in the range of 1 mg to 2000 mg. In particular the inventive pharmaceutical composition for oral dosage comprises per unit one or more inventive crystal salt forms of sulfasalazine in an amount of 10 mg, 20 mg, 25 mg, 30 mg, 40 mg, 50 mg, 60 mg, 70 mg, 75 mg, 80 mg, 90 mg, 100 mg, 110 mg, 120 mg, 125 mg, 130 mg, 140 mg, 150 mg, 160 mg, 170 mg, 175 mg, 180 mg, 190 mg, 200 mg, 210 mg, 220 mg, 225 mg, 230 mg, 240 mg, 250 mg, 260 mg, 270 mg, 275 mg, 280 mg, 290 mg, 300 mg, 310 mg, 320 mg, 325 mg, 330 mg, 340 mg, 350 mg, 360 mg, 370 mg, 375 mg, 380 mg, 390 mg, 400 mg, 410 mg, 420 mg, 425 mg, 430 mg, 440 mg, 450 mg, 460 mg, 470 mg, 475 mg, 480 mg, 490 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1,000 mg, 1,025 mg, 1,050 mg, 1,075 mg, 1,100 mg, 1,125 mg, 1,150 mg, 1,175 mg, 1,200 mg, 1,225 mg, 1,250 mg, 1,275 mg, 1,300 mg, 1,325 mg, 1,350 mg, 1,375 mg, 1,400 mg, 1,425 mg, 1,450 mg, 1,475 mg, 1,500 mg, 1,525 mg, 1,550 mg, 1,575 mg, 1,600 mg, 1,625 mg, 1,650 mg, 1,675 mg, 1,700 mg, 1,725 mg, 1,750 mg, 1,775 mg, 1,800 mg, 1,825 mg, 1,850 mg, 1,875 mg, 1,900 mg, 1,925 mg, 1,950 mg, 1,975 mg, 2,000 mg. Preferably, the dosage of one or all inventive crystal salt forms of sulfasalazine is lower than the single unit dosage of comparative pharmaceutical compositions comprising sulfasalazine free acid as alone. Accordingly, with respect to oral dosage forms (e.g. tablets, micro tablets, granules, powders, capsules, multi pellet unit systems) of the inventive pharmaceutical composition, the single unit dosage comprises preferably <500 mg, ≤450 mg, ≤400 mg, ≤375 mg, ≤250 mg of inventive crystal salt forms of sulfasalazine.

The inventive pharmaceutical composition may alternatively be in the form of liquid preparations for oral administration, e.g. in the form of syrups or suspensions. Pharmaceutical excipients comprised in such liquid preparations may comprise sugar and/or a mixture of ethanol, water, glycerol and propylene glycol, preferably buffered to a suitable pH. Optionally such inventive liquid preparation may contain one, two, three, four or more further excipients, preferably selected from the group consisting of colouring agents, flavouring agents, saccharine and/or carboxymethylcellulose as a thickening agent or other excipients known to those skilled in the art.

According to a further alternative or cumulative embodiment of the invention pharmaceutical composition the pharmaceutical composition may further comprise one, two, three or more further active ingredients, preferably selected from the group consisting of non-steriodal anti-inflammatory agents; preferably non-selective cyclo-oxygenase COX-1/COX-2 inhibitors whether applied topically or systemically, e.g. piroxicam, diclofenac, propionic acids such as naproxen, flurbiprofen, fenoprofen, ketoprofen and ibuprofen, fenamates such as mefenamic acid, indomethacin, sulindac, ayapropayone, pyrayoleones such as phenylbutazone, salicylates such as aspirin, selective COX-2 inhibitors, e.g. meloxicam, celecoxib, rofecoxib, valdecoxib, lumarocoxib, parecoxib and etoricoxib, cyclo-oxygenase inhibiting nitric oxide donors (CINODs); glucocorticoid, preferably flunisolide, triamcinolone acetonide, betamethasone dipropionate, budesonide, fluticasone propionate, ciclesonide or mometasone furoate; methotrexate; leflunomide; hydroxychloroquine; d-penicillamine; diacerein; nutritional supplements, preferably glucosamine; gold preparations, preferably auranofin; cytokine or agonist or antagonist of cytokine function; monoclonal antibody targeting B-Lymphocytes, preferably CD20 (rituximab); MRA-aIL16R; T-lymphocytes; CTLA4-Ig; HuMax 11-15; a modulator of chemokine receptor function, preferably an antagonist of CCR2, CCR2A, CCR2B, CCR3, CCR4, CCR5, CCR6, CCR7, CCR8, CCR9, CCRIO and CCRI I (for the C-C family), CXCRI, CXCR2, CXCR3, CXCR4 and CXCR5 (for the C-X-C family) and CX3CRI (for the C-X3-C family); azathioprine, tofacitinib, monoclonal antibodies, such as the anti tumour necrosis factor alpha monoclonal antibodies infliximab, adalimumab, and golimumab; interleukin 1 receptor antagonist, e.g. anakinra; etanercept, and abatacept; more preferably methotrexate and hydroxychloroquine. Alternatively or cumulatively, the inventive pharmaceutical composition may comprise sulfasalazine free acid form. Preferably the amount of sulfasalazine free acid form is less than the amount of the inventive crystal salt forms of sulfasalazine in the inventive pharmaceutical composition.

The inventive crystal salt forms of sulfasalazine and their in vivo metabolites sulfapyridine and 5-ASA are useful as modulators of function of various inflammatory cell types such as T cells, B cells, dendritic cells, neutrophils, NK cells and mast cells. For example, in experiments that studied the proliferation of human synovial cells of patients with rheumatoid arthritis, it was shown that the proliferation of these cells as well as the production of IL-1B and IL-6 by these cells were significantly inhibited. In these experiments it could be shown, that the overexpression of c-fos mRNA was inhibited by the inventive crystal forms of sulfasalazine. Thus, the inventive crystal forms of sulfasalazine may be administered to a mammal, including man, in particular for the treatment of autoimmune, inflammatory, proliferative and hyperproliferative diseases and immunologically-mediated diseases.

Thus, according to other embodiments of all aspects of the present invention the inventive pharmaceutical composition and the inventive crystal forms is/are for use in the treatment of
i) a disease or condition in which modulation of inflammatory cells is beneficial,
ii) a disease or condition concerning bones or joints, preferably selected from the group consisting of arthritis associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy, septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositis and polymyositis; polymyalgia rheumatic; juvenile arthritis including idiopathic inflammatory arthritis of whatever joint distribution and associated syndromes, and rheumatic fever and its systemic complications; vasculitis including giant cell arteritis, Takayasu's arteritis, Churg-Strauss syndrome, polyarteritis nodos, microscopic polyarteritis, and vasculitis associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthralgias, tendonitis, and myopathies; and iii) a disease or condition concerning gastro-intestinal tract, preferably selected from the group consisting of eosinophilic gastro-enteritis, mastocytosis, Crohn's disease, colitis including ulcerative colitis, proctitis; coeliac disease, irritable bowel syndrome, and food-related allergies which may have effects remote from the gut, e.g. migraine, rhinitis or eczema.

According to other aspects, the present invention relates to the use of inventive crystal salt forms of sulfasalazine or an inventive pharmaceutical composition in the preparation of a medicament for/in the treatment of above mentioned disorders or conditions.

According to another aspect, the present invention relates to a method of treating one or more of above mentioned disorders or conditions in a patient suffering from, or at risk of, said disease or condition, which comprises administering to the patient a therapeutically effective amount of an inventive crystal salt form of sulfasalazine or an inventive pharmaceutical composition.

According to all aspects, the present invention further relates to combination therapies wherein one or more inventive crystal salt forms of sulfasalazine or the inventive pharmaceutical composition is administered concurrently (simultaneously) or sequentially or as a combined pharmaceutical preparation or as a combined administration schedule with one or more active ingredients (therapeutic agents) for the treatment of one or more of the diseases and conditions, preferably the diseases and conditions listed above.

In the context of the present specification, the term 'therapy' also includes 'prophylaxis' unless there are specific indications to the contrary. The terms 'therapeutic' and 'therapeutically' should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

According to the inventive treatment of the inflammatory diseases as set out hereinbefore, the one, two, three, four or more inventive crystal salt forms of sulfasalazine or the inventive pharmaceutical composition may be used in the same or separate pharmaceutical compositions with one, two, three or more active ingredients (therapeutic agents), preferably selected from the group consisting of therapeutic agents as listed below:

Non-steroidal anti-inflammatory agents (hereinafter NSAIDs) including non-selective cyclooxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticoids (whether administered by topical, oral, intramuscular, intravenous, or intra-articular routes); methotrexate, leflunomide, hydroxychloroquine, d-penicillamine; auranofin and other parenteral or oral gold preparations; analgesics; diacerein; intra-articular therapies such as hyaluronic acid derivatives; and nutritional supplements such as glucosamine.

Cytokine or agonist or antagonist of cytokine function, (including agents which act on cytokine signaling pathways such as modulators of the SOCS system) including alpha-, beta-, and gamma-interferons; insulin-like growth factor type I (IGF-I); interleukins (IL) including IL-1 to 23, and interleukin antagonists or inhibitors such as anakinra; tumour necrosis factor alpha (TNF-α) inhibitors such as anti-TNF monoclonal antibodies (for example infliximab, adalimumab, and golimumab) and TNF receptor antagonists including immunoglobulin molecules (such as etanercept) and low-molecular-weight agents such as pentoxyfylline.

Monoclonal antibody targeting B-Lymphocytes (such as CD20 (rituximab). MRA-aIL16R and T-Lymphocytes, CTLA4-Ig, HuMax 11-15).

Modulator of chemokine receptor function such as an antagonist of CCR2, CCR2A, CCR2B, CCR3, CCR4, CCR5, CCR6, CCR7, CCR8, CCR9, CCRIO and CCRI I (for the C-C family); CXCRI, CXCR2, CXCR3, CXCR4 and CXCR5 (for the C-X-C family) and $CX_3CRI$ for the $C-X_3-C$ family.

Inhibitor of matrix metalloprotease (Tv-IMPs)$_5$ i.e., the stromefysins, the collagenases, and the gelatinases, as well as aggrecanase; especially collagenase-1 (MMP-I)$_5$ collagenase-2 (MMP-8), collagenase-3 (MMP-13), stromelysin-1 (MMP-3), stromelysin-2 (MMP-IO), and stromelysin-3 (MMP-11) and MMP-9 and MMP-12, including agents such as doxycycline.

Leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-213S; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAYx1005.

Receptor antagonist for leukotrienes (LT) B4, LTC4, LTD4, and LTE4. selected from the group consisting of the phenothiazin-3-Is such as L-651,392; amidino compounds such as CGS-25019c; benzoxalamines such as ontazolast; and compounds such as zafirlukast, ablukast, montelukast, pranlukast, verlukast (MK-679), RG-12525, Ro-245913, iralukast (CGP 45715A), and BAYx7195.

Phosphodiesterase (PDE) inhibitor such as a methylxanthanine including theophylline and aminophylline; a selective PDE isoenzyme inhibitor including a PDE4 inhibitor an inhibitor of the isoform PDE4D, such as apremilast or an inhibitor of PDE5.

Endothelin antagonist such as Tezosentan, Bosentan, Macitentan, Enrasentan, and Sixtasentan.

Angiotensin II antagonist such as Azilsartan, Losartan, Valsartan, Candesartan, and Telmisartan.

Dual antagonists for both angiotensin II and endothelin A receptors (DARAs), such as disclosed in WO2000001389 and WO2001044239.

Adenosine A2a agonist such as CGS-21680 and/or an adenosine A3 agonist such as IB-MECA and/or an adenosine A2b antagonist. The present invention further relates to the combination of a compound of the invention, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

Proton pump inhibitor (such as omeprazole) or a gastroprotective histamine type 2 receptor antagonist.

Antagonist of the histamine type 4 receptor.

Alpha-I/alpha-2 adrenoreceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethyl norepinephrine hydrochloride.

Anticholinergic agents including muscarinic receptor ($MI_5$ M2, and M3) antagonist such as atropine, hyoscine, glycopyrrolate, ipratropium bromide, tiotropium bromide, oxitropium bromide, pirenzepine or telenzepine.

Beta-adrenoceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof.

Chromone, such as sodium cromoglycate or nedocromil sodium. The present invention still further relates to the combination of a compound of the invention, with a glucocorticoid, such as flunisolide, triamcinolone acetonide, betamethasone dipropionate, budesonide, fluticasone propionate, ciclesonide or mometasone furoate.

Agent that modulates a nuclear hormone receptor such as PPARs.

Immunoglobulin (Ig) or Ig preparation or an antagonist or antibody modulating Ig function such as anti-IgE (for example omalizumab).

Another systemic or topically-applied anti-inflammatory agent, such as thalidomide or a derivative thereof, a retinoid, dithranol or calcipotriol.

Aminosalicylates and sulfapyridines such as sulfasalazine, mesalazine, balsalazide, and olsalazine; and immunomodulatory agents such as the thiopurines, and corticosteroids such as budesonide. Preferably, the amount of further aminosalicylates and sulfapyridine are less than the amount of the inventive crystal forms of sulfasalazine per unit dosage form.

Antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

Cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

Antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

Agent for the treatment of acute or chronic pain, such as a centrally or peripherally-acting analgesic (for example an opioid or derivative thereof), carbamazepine, phenytoin, sodium valproate, amitryptiline or other anti-depressant agent-s, paracetamol, or a non-steroidal anti-inflammatory agent.

A parenterally or topically-applied (including inhaled) local anaesthetic agent such as lignocaine or a derivative thereof.

anti-osteoporosis agent including a hormonal agent such as raloxifene, or a biphosphonate such as alendronate.

One or more agents selected from the following group: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Tofacitinib, Gefitinib or Imatinib mesylate), a serine/threonine kinase (such as an inhibitor of a MAP kinase such as p38, INK, protein kinase A, B or C, or inhibitors of kappaB kinases, such as $IKKI_5$ IKK2 or IKK3), or a kinase involved in cell cycle regulation (such as a cylin dependent kinase); (viii) glucose-6 phosphate dehydrogenase inhibitor; (ix) kinin-$B_1$-or $B_2$-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin $KK.sub1$. or $NK.sub3$. receptor antagonist such as NKP-608C, SB-233412 (talnetant) or D-441S; (xx) elastase inhibitor such as LT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2X7; or (xxvii) inhibitor of transcription factor activation such as NFkB, API, or STATS, (xxvii) agents modulating guanylate cyclase such as riociguat (methyl-N-[4,6-Diamino-2-[1-[(2-fluorphenyl) methyl]-1H-pyrazolo[3,4-b]pyridin-3-yl]-5-pyrimidinyl]-N-methyl-carbaminat (IUPAC)).

One or more therapeutic agents for the treatment of cancer, preferably selected from the group consisting of (i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil, ortegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere): or a topoisomerase inhibitor (for example an epipodophyllotoxin such as etoposide, teniposide, amsacrine, topotecan or a camptothecin); (ü) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, fhitamide, nilutamide or cyproterone acetate), a LHRH antagonist or LHRH agonist (for example goserelin, leuprorelin or biiserelin), a progestogen (for example megestrol acetate), an aromatase inhibitor (for example as anastrozole, letrozole, vorazole or exemestane) or an inhibitor of 5α-reductase such as finasteride; (iii) an agent which inhibits cancer cell invasion (for example a metalloproteinase inhibitor like marimastat or an inhibitor of urokinase plasminogen activator receptor function); (iv) an inhibitor of growth factor function, for example: a growth factor antibody (for example the anti-erbb2 antibody trastuzumab, or the anti-erbbI antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZDI 839), N-(3-ethynylphenyl)-6,7-bis(2-methoxyethoxy)quinazolin-4-amine (erlotinib. OSI-774) or 6-acrylamido-N-(3-chloro-4-fiuorophenyl)-7-(3-morpholinopropoxy)quinazolin-4-amine (CI 1033)), an inhibitor of the platelet-derived growth factor family, or an inhibitor of the hepatocyte growth factor family; (v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin); (vi) a vascular damaging agent such as combretastatin A4, or a compound disclosed in WO 99/02166, WO 00/40529, WO 00/41669, WO 01/92224, WO 02/04434 or WO 02/08213; (vii) an agent used in antisense therapy, for example one directed to one of the targets listed above, such as ISIS 2503, an anti-ras antisense; (viii) an agent used in a gene therapy approach, for example approaches to replace aberrant genes such as aberrant p53 or aberrant BRCAI or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

One or more therapeutic agents for the treatment of airway disease, respiratory disease and/or an inflammatory disease such as for example chronic obstructive pulmonary disease and asthma. The inventive crystal salt forms of sulfasalazine can be administered by inhalation or by the oral route and the agent for the treatment of airway disease, respiratory disease and/or an inflammatory disease such as for example chronic obstructive pulmonary disease and asthma (other agent) can independently be selected to be administered by inhalation or by the oral route. The inventive crystal salt forms of sulfasalazine and the other agent may be administered in one pharmaceutical formulation or in separate pharmaceutical formulations. In case of separate pharmaceutical formulations, the inventive crystal salt forms of sulfasalazine and the other agent may be administered simultaneously or sequentially or separately.

Dependent on the therapeutic uses, the dosage of the inventive crystal salt forms of sulfasalazine will, of course, vary with the mode of administration, the treatment desired and the disorder indicated, but may typically be in the range from 1 mg/kg to 50 mg/kg.

EXAMPLES

The present invention is described in the following on the basis of exemplary embodiments, which merely serve as examples and which shall not limit the scope of the present protective right. The exemplified features may be combined separately or in any (sub)combination with the general disclosure of all aspects of the invention hereinbefore.

General Methods $^1$H-NMR and $^{13}$C-NMR

The produced examples were characterized regarding identity and salt stoichiometry using proton and carbon nuclear magnetic resonance ($^1$H-NMR and $^{13}$C-NMR), regarding crystal modification by X-ray powder diffraction (XRPD), thermal properties by differential scanning calorimetry (DSC), water interactions by gravimetric vapour sorption (GVS), salt stoichiometry (HPLC), counter ion identity (CE) and at last by solubility in water (HPLC).

$^1$H NMR and $^{13}$C NMR spectra were recorded at 298K on a Varian Unity Inova 400 MHz (software: VKMR 6.1C and VNMRJ 1.1D; probe: Xalorac 5 mm DG400-5AT) or a Varian Mercury—VX 300 MHz (software: VNMR 6.1C; probe: Varian 5 mm AutoSW PFG) instrument. The central peaks of acetone-$d_6$ or dimethylsulphoxide (DMSO)-$d_6$ were used as internal references.

XRPD

X-ray powder diffraction (XRPD) analyses may be performed on samples prepared according to standard methods (see for example Giacovazzo et al., eds., Fundamentals of Crystallography, Oxford University Press (1992); Jenkins & Snyder, eds., Introduction to X-Ray Powder Diffractometry, John Wiley & Sons, New York (1996); Bunn, ed., Chemical Crystallography, Clarendon Press, London (1948); and Klug and Alexander, eds., X-Ray Diffraction Procedures, John Wiley & Sons, New York (1974): Precipitated samples were smeared out on a zero-background sample holder and analysed from 2-35° (2-teta) using a Thermo ARL X'tra diffractometer equipped with a peltier-cooled solid state detector, a Cu tube ($\lambda$=1.5418 Å), 45 kV/44 mA, using spinning sample holders and continuous scans with a scan speed of 2°/min and step size of 0.02°. The standard deviation is ±0.2° 2-theta (2θ).

DSC

Differential scanning calorimetry (DSC) using standard methods, for example those described in Höhne, G. W. H. et al (1996), Differential Scanning calorimetry, Springer, Berlin, the calometric response of a test sample to increasing temperature was investigated using a PerkinElmer Pyris DSC. The temperature interval was normally 60 to 285° C., with some variations depending on results and need of re-runs. The scanning rate was 10° C./min. About 2 mg sample was used; the measurements were performed using open aluminium pans and dry nitrogen atmosphere to avoid oxidative degradation. It is well known that the DSC onset and peak temperatures may vary due to the purity of the sample and instrumental parameters, especially the temperature scan rate. A person skilled in the art can use routine optimization/calibration to set up instrumental parameters for a DSC so that data comparable to the data presented here can be collected.

GVS

Gravimetric vapour sorption (GVS) was used to determine the hygrocopicity of the samples: experiments were performed at 25° C. using a DVS 1 instrument from SMS Ltd to record adsorption-desorption isotherms using different methods, the main features being: a single sorption/desorption cycle from 0 to 80% RH in 10% RH steps with a dm/dt trigger value of 0.002% (dm/dt=change in mass with time—when the balance stability is within this value the next step is automatically started, however, if those conditions are not achieved there is a default maximum time for each step of 6 hours). The sample amount used was 1-3 mg.

HPLC

The amount of dissolved sulfasalazine was determined by HPLC on an Agilent 1100 instrument, using a Waters XTerra 3.5 μm C18 column (50*4.6 mm) and a mobile phase consisting of 95% ethanol/25 mM phosphoric acid 45/55. The flow rate was 1.0 mL/min, injection volume 5 μL and detection wavelengths 358 nm (for assay) and 260 nm (for chromatographic purity). Quantitation was performed using external standard methodology. The assay method has been validated with respect to selectivity, repeatability and linearity.

CE

In Capillary Electrophoresis (CE), positive identity of the selected counterion was shown by corresponding migration times between sample and reference solution peaks. The instrument used was a Hewlett-Packard 3D-CE. The capillary was a fused silica 50 μm inner diameter and 56 cm efficient length. The electrolyte was Agilent Cation Buffer for CE (P.N. 5064-8203), the voltage 30 kV positive, injection 50 mbar*10 s (sample solutions), 25 mbar*3 s (reference solutions). Detection was performed using indirect UV-detection at 310 nm with a reference wavelength at 215 nm.

TGA

Thermal Gravimetric Analysis (TGA) Instrument: PerkinElmer TGA7 Method: About 3 mg of sample was charged into and weighed in an open Pt-pan and analyzed, in a flow of dry nitrogen gas to ensure an inert atmosphere, from 22 to 120° C. using a scan speed of 10° C./min, then held at 120° C. for 30 minutes.

Example 1

Preparation of D(−)-N-methylglucamine 2-hydroxy-5-[2-[4-[(2-pyridinylamino)sulfonyl]phenyl]diazenyl]-benzoate, crystal Form A Sulfasalazine (2.00 g, 5.0 mmol) and D(−)-N-methylglucamine (1.00 g, 5.1 mmol) were weighed into a 250 ml round-bottomed flask equipped with magnetic stirrer. Acetone (200 ml) was added and the mixture stirred at 60° C. The solid materials gradually dissolved and after a few hours a new precipitate started to form. The mixture was never completely dissolved. After 24 h at 60° C. tert-butyl methylether (40 ml) was added from a dropping funnel (5 min) and crystal seeds (1 mg Form A meglumine sulfasalazine salt obtained as described in Example 5) were added. After 30 min the heating was turned off and the mixture stirred another 60 h at ambient temperature. It was then filtered (Robu-Glas borosilicate glass filter porosity 3) and the solid washed with 20% mixture of tert-butyl methylether in acetone (50 ml). The material was dried 17 h in vacuo and weighed on the filter to give 2.92 g (97.4%) yellow crystalline powder. This material was analysed by 1H-NMR and found to contain 0.53% w/w acetone and traces of tert-butyl methylether (<0.02% w/w).

$^1$H NMR (400 MHz, DMSO-d6) δ 8.27 (d, J=2.7 Hz, 1H), 8.03-7.95 (m, 3H), 7.91-7.83 (m, 2H), 7.80 (dd, J=8.9, 2.7 Hz, 1H), 7.75 (ddd, J=8.9, 7.1, 1.9 Hz, 1H), 7.21 (d, J=8.7 Hz, 1H), 6.86 (t, J=6.6 Hz, 1H), 6.73 (d, J=8.9 Hz, 1H), 5.38 (s, 1H), 4.57 (s, 1H), 4.43 (s, 1H), 3.89-3.80 (m, 1H), 3.66 (dd, J=5.3, 1.6 Hz, 1H), 3.60 (dd, J=10.8, 3.2 Hz, 1H), 3.49 (dt, J=8.9, 4.2 Hz, 1H), 3.45-3.37 (m, 2H), 3.05 (dd, J=12.6, 3.3 Hz, 1H), 2.94 (dd, J=12.6, 9.5 Hz, 1H), 2.55 (s, 3H); $^{13}$C NMR (101 MHz, DMSO-d6) δ 170.96, 170.29, 154.12, 141.99, 127.70, 126.94, 126.78, 122.02, 119.07, 118.24, 71.28, 70.39, 70.10, 68.34, 63.27, 50.80; loss on drying (TGA; % w/w) is 0.2; melting point (DSC) is 163.5° C.±2.5° C. (onset); water vapor uptake (GVS; % w/w) at 30% RH is <0.4 and at 80% RH <0.9; solubility in de-ionized water at 24° C. and pH 6.6>54 mg/mL; stoichiometry, base to acid, of 1:1 was confirmed by NMR.

X-ray powder diffraction pattern of crystal Form A of the meglumine salt of sulfasalazine shown in FIG. 1, in particular comprising the following XRPD peaks (expressed as degrees 2θ±0.2 degress)

(10) 6.35, 13.93 and 22.41, or
(11) 9.31, 15.86 and 20.99, or
(12) 6.35, 13.93, 15.48, 15.86, 22.41 and 23.60, or
(13) 6.35, 10.79, 12.93, 13.93, 15.48, 15.86, 18.12, 19.82 and 22.41, or
(14) 9.31, 10.79, 12.93, 13.93, 14.47, 15.48, 15.86, 17.56, 19.10, 23.60 and 28.07, or
(15) 6.35, 12.93, 13.93, 14.47, 15.48, 15.86, 19.10, 19.82, 20.99, 21.27, 22.41, 23.60, 23.89 and 28.07, or
(16) 6.35, 9.31, 10.79, 12.93, 13.93, 14.47, 15.48, 15.86, 17.78, 18.12, 19.82, 20.11, 20.99, 21.27, 22.41, 23.60, 23.89, 28.07 and 28.80, or
(17) 6.35, 9.31, 10.79, 12.93, 13.93, 14.47, 15.48, 15.86, 17.56, 17.78, 18.12, 18.50, 19.10, 19.82, 20.11, 20.99, 21.27, 22.41, 23.60, 23.89, 24.70, 25.14, 25.55, 25.93, 26.81, 28.07 and 28.80, or
(18) 6.35, 9.31, 10.79, 12.93, 13.93, 14.47, 15.48, 15.86, 17.56, 17.78, 18.12, 18.50, 19.10, 19.82, 20.11, 20.99, 21.27, 22.41, 23.60, 23.89, 24.70, 25.14, 25.55, 25.93, 26.81, 28.07, 28.80, 29.49, 32.01, 32.58, 33.23.

Example 2

Preparation of D(−)-N-methylglucamine 2-hydroxy-5-[2-[4-[(2-pyridinylamino)sulfonyl]phenyl]diazenyl]-benzoate, inventive crystal Form A To a suspension of 30 mg sulfasalazine in acetone the equimolar amount of D(−)-N-methylglucamine (1 M stock solution in water) was added. The suspension was heated to 23° C. and the resulting solution stirred for 4 days, after which the solvent was slowly evaporated. The salt product was washed and filtered to dryness, yielding the polymorph named form A D(−)-N-methylglucamine 2-hydroxy-5-[2-[4-[(2-pyridinylamino)sulfonyl]phenyl]diazenyl]-benzoate.

$^1$H-NMR (400 MHz, DMSO-d$_6$) δ 8.27 (d, J=2.7 Hz, 1H), 8.05-7.95 (m, 3H), 7.91-7.83 (m, 2H), 7.80 (dd, J=8.8, 2.7 Hz, 1H), 7.75 (ddd, J=8.9, 7.2, 1.9 Hz, 1H), 7.21 (d, J=8.7 Hz, 1H), 6.86 (t, J=6.6 Hz, 1H), 6.73 (d, J=8.8 Hz, 1H), 5.37 (s, 1H), 4.57 (s, 1H), 4.44 (s, 1H), 3.88-3.80 (m, 1H), 3.66 (dd, J=5.2, 1.6 Hz, 1H), 3.60 (d, J=10.7 Hz, 1H), 3.53-3.37 (m, 3H), 3.05 (dd, J=12.6, 3.4 Hz, 1H), 2.94 (dd, J=12.6, 9.5 Hz, 1H), 2.56 (s, 3H); $^{13}$C-NMR (101 MHz, DMSO-d$_6$) δ 171.01, 170.25, 154.13, 141.97, 127.70, 126.93, 126.78, 122.01, 119.06, 118.25, 71.28, 70.38, 70.09, 68.31, 63.26, 50.78, 40.12, 33.04; melting point (DSC): 160° C.±2° C. (onset); water vapor uptake (GVS; % w/w) at 30% RH is 0.4; at 80% RH is 1.1; stoichiometry, base to acid, of 1:1 was confirmed by NMR and HPLC.

X-ray powder diffraction pattern of crystal Form A of the meglumine salt of sulfasalazine shown in FIG. 1, in particular comprising the following XRPD peaks (expressed as degrees 2θ±0.2 degress)

(1) 6.35, 13.93 and 22.41, or
(2) 9.31, 15.86 and 20.99, or
(3) 6.35, 13.93, 15.48, 15.86, 22.41 and 23.60, or
(4) 6.35, 10.79, 12.93, 13.93, 15.48, 15.86, 18.12, 19.82 and 22.41, or
(5) 9.31, 10.79, 12.93, 13.93, 14.47, 15.48, 15.86, 17.56, 19.10, 23.60 and 28.07, or
(6) 6.35, 12.93, 13.93, 14.47, 15.48, 15.86, 19.10, 19.82, 20.99, 21.27, 22.41, 23.60, 23.89 and 28.07, or
(7) 6.35, 9.31, 10.79, 12.93, 13.93, 14.47, 15.48, 15.86, 17.78, 18.12, 19.82, 20.11, 20.99, 21.27, 22.41, 23.60, 23.89, 28.07 and 28.80, or
(8) 6.35, 9.31, 10.79, 12.93, 13.93, 14.47, 15.48, 15.86, 17.56, 17.78, 18.12, 18.50, 19.10, 19.82, 20.11, 20.99, 21.27, 22.41, 23.60, 23.89, 24.70, 25.14, 25.55, 25.93, 26.81, 28.07 and 28.80, or
(9) 6.35, 9.31, 10.79, 12.93, 13.93, 14.47, 15.48, 15.86, 17.56, 17.78, 18.12, 18.50, 19.10, 19.82, 20.11, 20.99, 21.27, 22.41, 23.60, 23.89, 24.70, 25.14, 25.55, 25.93, 26.81, 28.07, 28.80, 29.49, 32.01, 32.58, 33.23.

Example 3

Preparation of piperazine 2-hydroxy-5-[2-[4-[(2-pyridinylamino)sulfonyl]phenyl]diazenyl]-benzoate, inventive crystal Form A To a suspension of 30 mg sulfasalazine in methanol the equimolar amount of piperazine (1 M stock solution in water) was added. The suspension was heated to 23° C. and stirred for 4 days. The salt product was then filtered, washed and filtered again to dryness, yielding the polymorph named Form A piperazine sulfasalazine.

$^1$H-NMR (400 MHz, DMSO-d$_6$) δ 8.28 (d, J=2.7 Hz, 1H), 8.00 (dt, J=6.9, 2.1 Hz, 3H), 7.88 (d, J=8.6 Hz, 2H), 7.84 (dd, J=8.8, 2.7 Hz, 1H), 7.75 (ddd, J=8.9, 7.2, 1.9 Hz, 1H), 7.21 (d, J=8.7 Hz, 1H), 6.86 (t, J=6.4 Hz, 1H), 6.79 (d, J=8.8 Hz, 1H), 3.18 (s, 8H); $^{13}$C-NMR (101 MHz, DMSO-d$_6$) δ 170.55, 169.77, 154.01, 142.36, 127.71, 127.22, 126.65, 122.10, 118.49, 118.22, 41.14; melting point (DSC): 270° C.±2° C. (heat rate 100 K/min); water vapor uptake (GVS; % w/w) at 30% RH is 0.4; at 80% RH is 0.9; solubility in de-ionized water at 24° C. after 24 h: 0.12 mg/mL; stoichiometry, base to acid, of 1:2 was confirmed by NMR and HPLC.

X-ray powder diffraction pattern of crystal Form A of the piperazine salt of sulfasalazine shown in FIG. 2, in particular comprising the following XRPD peaks (expressed as degrees 2θ±0.2 degress)

(1) 11.95, 12.30 and 16.42, or
(2) 12.30, 12.93 and 15.00, or
(3) 11.95, 12.30, 12.93, 16.42, 17.87 and 20.36, or
(4) 8.11, 11.95, 12.30, 15.01, 16.42, 17.87, 20.36 and 20.74, or
(5) 11.95, 12.30, 12.93, 15.01, 16.42, 17.87, 20.36, 20.74, 22.41 and 23.41 or
(6) 11.95, 15.01, 16.42, 17.87, 20.36, 20.74, 23.41, 24.01, 24.67, 24.99 and 26.09, or (7) 8.11, 11.95, 12.30, 12.93, 15.01, 16.42, 17.87, 20.36, 20.74, 22.41, 23.41, 24.01, 24.67, 24.99 and 26.09, or
(8) 11.95, 12.30, 12.93, 15.01, 16.42, 17.87, 20.36, 20.74, 22.41, 23.41, 24.01, 24.67, 24.99, 26.09, 26.81, 27.73 and 28.80, or
(9) 8.11, 11.95, 12.30, 12.93, 15.01, 16.42, 17.87, 20.36, 20.74, 22.41, 23.41, 24.01, 24.67, 24.99, 26.09, 26.81, 27.73, 28.80, 29.80 and 30.43.

Example 4

Preparation of diethylamine 2-hydroxy-5-[2-[4-[(2-pyridinylamino)sulfonyl]phenyl]diazenyl]-benzoate, crystal Form A not covered by the present invention To a suspension of 30 mg sulfasalazine in acetonitrile the equimolar amount of diethylamine (1 M stock solution in water) was added. The suspension was heated to 23° C. and stirred for 4 days. The salt product was then filtered, washed and filtered again to dryness, yielding the polymorph named form A diethylamine sulfasalazine.

$^1$H-NMR (400 MHz, DMSO-$d_6$) δ 8.26 (d, J=2.7 Hz, 1H), 8.02-7.95 (m, 3H), 7.87 (d, J=8.3 Hz, 2H), 7.79 (dd, J=8.9, 2.7 Hz, 1H), 7.75 (t, J=8.7, 7.6 Hz, 1H), 7.21 (d, J=8.6 Hz, 1H), 6.86 (s, 1H), 6.72 (d, J=8.8 Hz, 1H), 2.93 (q, J=7.3 Hz, 4H), 1.16 (t, J=7.3 Hz, 6H); $^{13}$C-NMR (101 MHz, DMSO-$d_6$) δ 170.21, 141.91, 126.91, 126.79, 121.99, 119.06, 118.27, 41.35, 11.05; melting point (DSC): 200° C.±2° C. (heat rate 10 K/min); water vapor uptake (GVS; % w/w) at 30% RH is 0.3; at 80% RH is 0.5; solubility in de-ionized water at 24° C. after 24 h: >0.31 mg/mL; stoichiometry, base to acid, of 1:1 was confirmed by NMR and HPLC.

X-ray powder diffraction pattern of crystal Form A of the diethylamine salt of sulfasalazine shown in FIG. 3, in particular comprising the following XRPD peaks (expressed as degrees 2θ±0.2 degress)
(1) 7.16, 11.48, and 18.78, or
(2) 10.50, 15.41 and 21.87, or
(3) 7.16, 10.50, 11.48, 18.78, 21.65 and 21.87, or
(4) 10.50, 11.48, 12.42, 14.38, 15.41, 16.64, 18.78 and 21.87, or
(5) 7.16, 10.50, 11.01, 11.48, 13.87, 15.92, 16.64, 18.78, 21.08, 21.65 and 22.15, or
(6) 7.16, 10.50, 11.01, 11.48, 12.42, 13.87, 14.38, 15.41, 15.92, 16.64, 17.19, 18.28, 18.78, 21.08, 21.65, 21.87, and 22.15 or
(7) 7.16, 10.50, 11.48, 12.42, 13.87, 14.38, 15.41, 15.92, 16.64, 20.52, 21.08, 21.65, 21.87, 22.15, 22.47, 23.16, 23.63, 24.14 and 25.11, or
(8) 7.16, 10.50, 11.01, 11.48, 12.42, 13.87, 14.38, 15.41, 15.92, 16.64, 17.19, 18.28, 18.78, 20.52, 21.08, 21.65, 21.87, 22.15, 22.47, 23.16, 23.63, 24.14 and 25.11, or
(9) 7.16, 10.50, 11.01, 11.48, 12.42, 13.87, 14.38, 15.41, 15.92, 16.64, 17.19, 18.28, 18.78, 20.52, 21.08, 21.65, 21.87, 22.15, 22.47, 23.16, 23.63, 24.14, 25.11, 26.94, 27.95, 28.92, 29.46.

Example 5

Preparation of diethylamine 2-hydroxy-5[2-[4-[(2-pyridinylamino)sulfonyl]phenyl]diazenyl]-benzoate, inventive crystal Form B 25 mg sulfasalazine was added to 5 ml acetone was added and a solution containing 10% excess of the counter ion diethylamine in acetone was added. The mixture was heated to 45° C., and the solvent slowly evaporated, resulting in the polymorph named Form B diethylamine sulfasalazine salt.

X-ray powder diffraction pattern of crystal Form B of the diethylamine salt of sulfasalazine shown in FIG. 4, in particular comprising the following XRPD peaks (expressed as degrees 2θ±0.2 degress)
(1) 6.85, 17.82 and 22.75, or
(2) 11.38, 20.58 and 23.98, or
(3) 6.85, 11.38, 17.82, 20.58 and 22.75, or
(4) 6.85, 11.38, 11.70, 17.62, 20.58, 22.75 and 23.98, or
(5) 11.38, 11.70, 15.29, 16.71, 17.62, 19.92, 20.58, 21.30, 22.75, 23.63 and 23.98, or
(6) 6.85, 11.38, 11.70, 14.78, 15.29, 15.70, 16.71, 17.62, 19.92, 20.20, 20.58, 21.30, 22.75, 23.63, 23.98 and 28.61 or
(7) 6.85, 11.38, 11.70, 14.78, 15.29, 15.70, 16.71, 17.62, 19.92, 20.20, 20.58, 21.30, 22.75, 23.63, 23.98, 25.05, 25.71, 26.81, 27.95 and 28.61, or
(8) 6.85, 11.38, 11.70, 14.78, 15.29, 15.70, 16.71, 17.62, 19.92, 20.20, 20.58, 21.30, 22.75, 23.63, 23.98, 25.05, 25.71, 26.81, 27.95, 28.61, 29.14, 31.06.

Example 6

Comparison of Transport Rates of Sulfasalazine Free Acid Form and the Crystal Form A Meglumine Salt of Sulfasalazine Across Caco 2 Cell Monolayer For the transport experiments, Caco-2 cells were seeded with a density of 67800 cells per square centimeter on Transwell™ filter inserts, which were placed into 12-well flat bottom cluster plates. The inserts (apical compartments) were supplied with 0.5 mL and the outer wells (basal compartments) with 1.5 mL of DMEM culture medium. The cells were cultured at 37° C., 10% CO2 and 90% relative humidity in DMEM culture medium for 14 to 30 days until they formed confluent monolayers. Confluency and tightness of the cell monolayer were checked by measuring the transepithelial electrical resistance using an EVOM™ voltohmmeter with STX-2 electrode. Monolayers were rejected if the TEER was lower than 200 Ω*cm$^2$ after pre-incubation (30 min) or after completion of the transport study. Test items were prepared according to the Biopharmaceutics Classification System (BCS) guidelines. Experiments were performed in triplicate. Immediately prior to the transport experiment, the cells were washed twice with Krebs-Ringer and the buffer was then replaced by the transport solutions. After 30 min pre-incubation, samples were withdrawn from both donor and acceptor compartments. Six samples were taken in total at t=0, 30, 60, 90, 120 and 180 min. The efflux ratio is calculated as the $P_{app}$ (ba)/$P_{app}$ (ab), where $P_{app}$ (ba) is the apparent permeability coefficient for the transport of the test compound from the basal to the apical side (secretive direction) and the $P_{app}$ (ab) is the apparent permeability coefficient for the transport of the test compound from the apical to the basal side (absorptive direction). The apparent permeability coefficient $P_{app}$ (in cm/s) was calculated as the permeability rate at steady state (in μg/s)*(1/initial mass of test compound in donor compartment (in μg)*1/area of the exposed cell monolayer (in cm$^2$)*buffer volume of donor compartment (in cm$^3$).

TABLE 1

Cumulative transport (μg/cm2) and $P_{app}$ values (E−06 cm/s) with relative standard deviations (RSD; %) after 180 min incubation

| Compound | Amount μg/mL | Transport direction | $P_{app}$ E−06 cm/s | RSD (%) | Cumulative drug transport μg/cm² | RSD (%) |
|---|---|---|---|---|---|---|
| Form A meglumine salt | 50 | ab | 2.16 | 30.6 | 2.38 | 38.2 |
| | 200 | ab | 4.17 | 16.1 | 12.77 | 10.4 |
| sulfasalazine | 50 | ab | 1.39 | 18.3 | 1.14 | 3.8 |
| | 200 | ab | 1.16 | 35.8 | 3.81 | 35.1 |

Table 1 shows that a higher amount of crystal Form A of the meglumine salt of sulfasalazine is cumulatively transported across Caco 2 cell monolayer. The ratio of the apparent permeation of sulfasalazine and of the Form A meglumine salt ranges from 1.5 (50 μg/mL) to 3.6 (200 μg/mL).

Example 7

Comparison of Pharmacokinetics of Sulfasalazine in Rat as Either the Free Acid Form or as Crystal Form A Meglumine Salt Following Intra Venous or Oral Administration

LIST OF ABBREVIATIONS

AUCinf.: Area under the curve to infinity; AUClast.: Area under the curve to the last data point; Cmax: Maximum concentration; CMC: Cyclic Methyl Cellulosa; F: Bioavailability; I.V.: Intra venous, LC: Liquid Chromatography; MS: Mass Spectrometry; NCA: Non Compartmental analysis; PK: Pharmacokinetic; P.O: Per os; SSZ: Sulfasalazine; TI: Test Item; Tmax: Time of maximum concentration; $T_{1/2}$: Half life In Vivo Study Protocol In accordance with Swedish legislations for preclinical in vivo studies in rodents and following evaluation and approval of the experimental procedures the local ethical committee (M388-12), following acclimatization to the housing conditions for a minimum of 7 days after arrival, male Wistar (Hannover) rats (Taconic, Denmark), average weight 180-200 g; average age 8-10 weeks, were treated with test items (see Fehler! Verweisquelle konnte nicht gefunden werden.); 12-16 h prior to dosing all food except for an amount equivalent to a half day consumption was removed. The test items were administrated using a soft gavage tube (p.o.) or by injecting the test item in the tail vein (i.v). The volume given was 10 mL/kg (p.o.) or 1 mL/kg (i.v.). Before i.v administration the rats were anesthetized using isoflurane. The rats were conscious during sample collection and the blood was taken from the sub-lingual vein. Blood samples were collected from each rat over a period of up to 24 h. At each time point two aliquots of 50 μL each was added to a vial containing 150 μL of sterile water. The samples were mixed immediately and stored in −18° C. until preparation for bioanalysis commenced. All formulations were prepared on the same day that dosing took place. The body weight of the rat was recorded before dosing. The weight of the syringe was recorded before and after administration to allow calculation of the actual amount of test sample delivered. The actual doses were used during the evaluation of the data.

TABLE 2

Study design

| Group | Route | Dose | Test item |
|---|---|---|---|
| Form A meglumine salt | i.v. | 1 mg/kg | 1.5 mg/mL in 0.9% NaCl (saline) |
| sulfasalazine | i.v. | 5 mg/kg | 7.5 mg/mL in 0.9% NaCl (saline) |
| Form A meglumine salt | p.o. | 60 mg/kg | 9 mg/mL in Phosphate buffer, 0.5% CMC, pH 7.4 |
| sulfasalazine | p.o. | 60 mg/kg | 6 mg/mL in Phosphate buffer, 0.5% CMC, pH 7.4 |

Bioanalysis

The plasma levels of sulfasalazine were determined using LCMS/MS in mrm (multiple reaction monitoring) mode.

Samples and standards were injected by a HTC PAL from CTC analytics into an LC system from Shimadzu consisting of a high pressure gradient system of two LC-10 AD pumps controlled by a SCL-10A controller from Shimadzu. The samples were separated using reverse-phase chromatography with gradient elution at a flow rate of 0.8 mL/min. Mobile phases were A:94.9/5/0.1 water/acetonitrile/formic acid and B:5/94.9/0.1 water/acetonitrile/formic acid. Gradient started at 0% B and increased linearly to 100% B in 4 minutes, 100% B was kept for 0.5 minutes and then the system returned to 0% B in 0.1 minutes. The system was equilibrated for 1.4 minutes until the total run time of 6 minutes. The eluent was analyzed by a Quattro Ultima from Micromass equipped with an electrospray ion source. Data was collected and calibrations were calculated by MassLynx 4.0 software. Sulfasalazine was separated on a Waters Symmetry C18 50×2.1 column. The eluent was ionized by negative ion electrospray and the mrm transition from 397 to 197 m/z was monitored.

The diluted blood sample (50 μL blood, 150 μL water) was thawed and mixed. 400 μL of Acetonitrile, to precipitate the protein was added and mixed again. The sample was centrifuged at 5,000 g for 5 minutes. 100 μL of the supernatant was transferred to a 300 μL glass vial and 100 μL of water was added to reduce the acetonitrile concentration.

Positive and negative mode MS/MS was employed for sulfasalazine. The concentration of the standard curve was in the range from 5 nM to 15625 nM. Samples with analyte concentrations above the upper limit of quantification were diluted with matrix to reach within the assay range. A non-compartmental analysis (NCA) was performed using the Phoenix WinNonLin analysis tool.

Results

Intravenous Administration

The pharmacokinetic profile for Sulfasalazine following i.v. administration of the Form A meglumine salt of sulfasalazine at 1 and 5 mg/kg is summarised in Table 3. There is a reasonable linearity of exposure between the two doses and the estimated half-life is 1.2 and 1.3 h respectively, which is in good consistence with published data (Zamek-Gliszczynski M J et al. Characterization of SAGE Mdr1a (P-gp), Bcrp, and Mrp2 knockout rats using loperamide, paclitaxel, sulfasalazine, and carboxydichlorofluorescein pharmacokinetics. Drug Metab Dispos 2012, 40, 1825).

TABLE 2

Pharmacokinetic profile of sulfasalazine following i.v. administration of the Form A meglumine salt of sulfasalazine

| SSZ Form A meglumine AUC$_{inf}$ obs (h*nM) | | SSZ Form A meglumine T$_{1/2}$ (h) | |
|---|---|---|---|
| 1 mg/kg | 5 mg/kg | 1 mg/kg | 5 mg/kg |
| 1,661 ± 191 | 11,889 ± 735 | 1.2 ± 0.2 | 1.3 ± 0.1 |

Oral Administration

The pharmacokinetic profile for sulfasalazine following p.o. administration of 60 mg/kg are summarised in Table 4. The maximum concentration of sulfasalazine is 7-fold increased for D(−)-N-methylglucamine 2-hydroxy-5-[2-[4-[(2-pyridinylamino)sulfonyl]phenyl]diazenyl]-benzoate, Form A as compared to sulfasalazine and is reached 6 times faster with D(−)-N-methylglucamine 2-hydroxy-5-[2-[4-[(2-pyridinylamino)sulfonyl]phenyl]diazenyl]-benzoate, Form A as compared to sulfasalazine. The total plasma level of sulfasalazine are increased with >50% (AUC$_{inf}$) and with >90% during the first 90 minutes following oral administration of the meglumine salt as compared to the free acid of sulfasalazine. The bioavailability of the Form A meglumine salt of sulfasalazine in rats is about 50% increased versus the bioavailability of the sulfasalazine in free acid form.

TABLE 3

Pharmacokinetic profile of sulfasalazine as following p.o. administration of the either Form A meglumine salt of sulfasalazine or of sulfasalazine as the free acid form.

| Group | T$_{max}$ (h) | C$_{max}$ (mM) | AUC$_{0-1.5\,h}$ obs (h*mM) | AUC$_{all}$ (h*mM) | T$_{1/2}$ (h) | F(%) |
|---|---|---|---|---|---|---|
| sulfasalazine | 0.72 ± 0.57 | 0.70 ± 0.11 | 0.81 ± 0.13 | 2.81 ± 0.41 | 2.0 ± 0.5 | 2.5 |
| Form A meglumine salt | 0.12 ± 0.05 | 5.20 ± 0.42 | 1.55 ± 0.52 | 4.23 ± 1.01 | 1.9 ± 0.5 | 3.8 |

Example 8

Comparison of Solubility Rates of Sulfasalazine Free Acid Form and the Crystal Form A Meglumine Salt of Sulfasalazine

HPLC

The amount of dissolved sulfasalazine was respectively determined by HPLC on an HP 1100 instrument, using a Waters X-Bridge 3.5 μm C18 column (150*4.6 mm) and a gradient method. The mobile phase consists of mobile phase (A): 1.13 g sodium dihydrogen phosphate and 2.5 g sodium acetate are dissolved in 1000 mL purified water. The pH is afterwards adjusted with acetic acid (100%) to 4.8. and mobile phase (B): 1 part mobile phase A is mixed with 4 parts of methanol for chromatography. The flow rate was 1.0 mL/min, injection volume 5 μL and detection wave-lengths 320 nm (HP DAD series 1100). Run time is 10 min. Quantitation was performed using external standard methodology. The assay method has been validated with respect to selectivity, repeatability and linearity. Samples are prepared with dilute ammonia R3 PhEur.

50 mg of sulfasalazine and Form A meglumine salt of sulfasalazine are respectively weighed into a 4 mL glass vial containing 2 mL water or FaSSIF-V2 medium and stirred at room temperature (20-25° C.) for 24 h, after which 20 mg of sulfasalazine and Form A meglumine salt were respectively additionally added until a saturated solution was obtained. The saturated solutions were filtrated using centrifuge filters (Nylon, 0.45 μM) and the clear supernatants were respectively injected either directly or after dilution with dilute ammonia R3 PhEur.

TABLE 5

| | Water | | FaSSIF-V2 | |
|---|---|---|---|---|
| Group | pH | Solubility (mg/mL) | pH | Solubility (mg/mL) |
| sulfasalazine | 5.9 | 0.06 | 6.3 | 0.78 |
| Form A meglumine salt | 7.5 | 104.8 | 6.4 | 15.3 |
| | 6.0* | 60.3 | n.a. | n.a. |

*diluted in phosphate Buffer pH 6.8

The invention claimed is:

1. A crystal meglumine salt of Form A of 2-hydroxy-5-[2-[4-[(2-pyridinylamino)sulfonyl]phenyl]diazenyl]-benzoic acid (sulfasalazine) wherein the crystal is characterized by peaks in the powder x-ray diffraction at values (±0.2) of two theta of 6.35, 13.93, 15.48, 15.86, 20.99, 22.41, 23.60 and 28.07, and wherein the crystals contain 0 to less than 5 wt.-% solvate and/or water based on the total weight of the crystal meglumine salt of Form A of sulfasalazine.

2. A pharmaceutical composition comprising a therapeutically effective amount of one or more of the crystal meglumine salts of Form A of sulfasalazine as claimed in claim 1.

3. The pharmaceutical co position according to claim 2, wherein the composition is formulated for oral or rectal administration.

4. The pharmaceutical composition according to claim 2, wherein the pharmaceutical composition further comprises one, two, three or more active ingredients selected from the group consisting of non-steriodal anti-inflammatory agents selected from preferably non-selective cyclo-oxygenase COX-1/COX-2 inhibitors whether applied topically or systemically selected from piroxicam, diclofenac, propionic acids selected from naproxen, flurbiprofen, fenoprofen, ketoprofen and ibuprofen, fenamates selected from mefenamic acid, indomethacin, sulindac, ayapropayone, pyrayoleones such as phenylbutazone, salicylates selected from aspirin, selective COX-2 inhibitors selected from meloxicam, celecoxib, rofecoxib, valdecoxib, lumarocoxib, parecoxib and etoricoxib, cyclo-oxygenase inhibiting nitric oxide donors (CINODs); glucocorticoid selected from flunisolide, triamcinolone acetonide, betamethasone dipropionate, budesonide, fluticasone propionate, ciclesonide or mometasone furoate; methotrexate; leflunomide; hydroxychloroquine; d-penicillamine; diacerein; nutritional supplements selected from glucosamine; gold preparations, preferably auranofin; cytokine or agonist or antagonist of cytokine function; monoclonal antibody targeting B-preferably selected from CD20 (rituximab); MRA-aIL16R; T-lymphocytes; CTLA4-Ig; HuMax 11-15; a modulator of chemokine receptor function selected from an antagonist of CCR2, CCR2A, CCR2B, CCR3, CCR4, CCR5, CCR6, CCR7, CCR8, CCR9, CCR1O and CCMI1 (for the C-C family), CXCR1, CXCR2, CXCR3, CXCR4 and CXCR5 (for the C-X-C family) and CX3CR1 (for the C-X3-C family); azathioprine, tofacitinib, monoclonal antibodies selected from the anti tumour necrosis factor alpha monoclonal antibodies infliximab, adalimumab, and golimumab; interleukin 1 receptor antagonist selected from anakinra; etanercept, and abatacept selected from methotrexate and hydroxychloroquine.

5. The pharmaceutical composition according to claim 2 for use in the treatment of
   i) A disease or condition in which modulation of inflammatory cells is beneficial;
   ii) A disease or condition concerning bones or joints selected from the group consisting of arthritis associated with or including osteoarthritis/osteoarthrosis, both primary and secondary to congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy, septic arthritis and other infection-related arthopathies and bone disorders selected from tuberculosis, including Potts' disease and Ponces syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositis and polymyositis; polymyalgia rheumatic; juvenile arthritis including idiopathic inflammatory arthritis of whatever joint distribution and associated syndromes, and rheumatic fever and its systemic complications; vasculitis including giant cell arteritis, Takayasu's arteritis, Churg-Strauss syndrome, polyarteritis nodus, microscopic polyarteritis, and vasculitis associated with viral infection, hypersensitivity reactions, cryoglobulins, and paraproteins; low back pain; Farriilial Mediterranean fever, Muckle-Wells syndrome, and Familial Hibernian Fever, Kikuchi disease; drug-induced arthralgias, tendonitis, and myopathies; or
   iii) A disease or condition concerning gastro-intestinal tract selected from the group consisting of eosinophilic gastro-enteritis, mastocytosis, Crohn's disease, olitrs including ulcerative colitis, proctitis; coeliac disease, irritable bowel syndrome, and food-related allergies which may have effects remote from the gut selected from migraine, rhinitis or eczema.

6. A crystal meglumine salt of Form A of sulfasalazine according to claim 2, wherein the crystals are characterized by peaks in the powder x-ray diffraction at values (±0.2) of two theta of 6.35, 13.93, 15.48, 15.86, 20.99, 22.41, 23.60 and 28.07, preferably have an X-ray powder diffraction pattern as that shown in FIG. 1.

7. The crystal meglumine salt as claimed in claim 1, wherein the crystals contain 0 to less than 4 wt.-% solvate and/or water based on the total weight of the crystal meglumine salt of Form A of sulfasalazine.

8. The crystal meglumine salt as claimed in claim 1, wherein the crystals contain 0 to less than 3 wt.-% solvate and/or water based on the total weight of the crystal meglumine salt of Form A of sulfasalazine.

9. The crystal meglumine salt as claimed in claim 1, wherein the crystals contain 0 to less than 2 wt.-% solvate and/or water based on the total weight of the crystal meglumine salt of Form A of sulfasalazine.

10. The crystal meglumine salt as claimed in claim 1, wherein the crystals contain 0 to less than 1 wt.-% solvate and/or water based on the total weight of the crystal meglumine salt of Form A of sulfasalazine.

\* \* \* \* \*